(12) United States Patent
Yeh

(10) Patent No.: US 12,427,262 B2
(45) Date of Patent: Sep. 30, 2025

(54) COMMON INJECTION DEVICE

(71) Applicant: CC BIOTECHNOLOGY CORPORATION, Tainan (TW)

(72) Inventor: Chin-Min Yeh, Tainan (TW)

(73) Assignee: CC BIOTECHNOLOGY CORPORATION, Tainan (TW)

( * ) Notice: Subject to any disclaimer, the term of this patent is extended or adjusted under 35 U.S.C. 154(b) by 456 days.

(21) Appl. No.: 17/641,996

(22) PCT Filed: Sep. 19, 2019

(86) PCT No.: PCT/CN2019/106677
§ 371 (c)(1),
(2) Date: Mar. 10, 2022

(87) PCT Pub. No.: WO2021/051350
PCT Pub. Date: Mar. 25, 2021

(65) Prior Publication Data
US 2024/0042134 A1  Feb. 8, 2024

(51) Int. Cl.
*A61M 5/28* (2006.01)
*A61M 5/20* (2006.01)
(Continued)

(52) U.S. Cl.
CPC .............. *A61M 5/281* (2013.01); *A61M 5/20* (2013.01); *A61M 5/31576* (2013.01);
(Continued)

(58) Field of Classification Search
CPC ...... A61M 5/20; A61M 5/281; A61M 5/3135; A61M 5/31576; A61M 5/31583;
(Continued)

(56) References Cited

U.S. PATENT DOCUMENTS 3,756,456 A * 9/1973 Georgi .................... G01G 19/64
                                                      73/1.22
3,796,163 A * 3/1974 Meyer .................... B23Q 41/06
                                                      104/88.04
(Continued)

FOREIGN PATENT DOCUMENTS

CN       101035579 A       9/2007
CN       102137691 A       7/2011
(Continued)

OTHER PUBLICATIONS

Frigyes, Myers, and Allison. "Fundamentals of Photoelectric Sensors", Jun. 13, 2010, automation.com. . https://www.automation.com/en-us/articles/2014-1/fundamentals-of-photoelectric-sensors (Year: 2010).*

(Continued)

*Primary Examiner* — Jason E Flick
*Assistant Examiner* — Isabella S North
(74) *Attorney, Agent, or Firm* — BACON&THOMAS,PLLC

(57) ABSTRACT

A common injection device is assembled with an injection needle containing a drug, and has a needle bushing, a drug-information providing portion disposed on the needle bushing, and an injection propulsion mechanism detachably connected to the needle bushing. The needle bushing has a connecting portion with multiple engaging hooks, a bushing base, and a middle hole. The needle bushing is assembled with the injection needle, and the drug-information providing portion provides readable drug information of the drug. The injection propulsion mechanism is used to connect the needle bushing, and the injection action is performed according to the drug information to ensure the safety of injection. The injection propulsion mechanism is of a general type and is reusable, and it is not necessary to make a specific or dedicated injection device according to the injec- (Continued)

tion needles equipped with different drugs, thereby reducing waste and reducing cost.

18 Claims, 19 Drawing Sheets

(51) Int. Cl.
*A61M 5/315* (2006.01)
*A61M 5/32* (2006.01)
*A61M 5/31* (2006.01)

(52) U.S. Cl.
CPC ......... *A61M 5/3286* (2013.01); *A61M 5/3135* (2013.01); *A61M 2005/3142* (2013.01); *A61M 5/31583* (2013.01); *A61M 2005/31588* (2013.01); *A61M 2205/103* (2013.01); *A61M 2205/502* (2013.01); *A61M 2205/6018* (2013.01); *A61M 2205/6027* (2013.01); *A61M 2205/6054* (2013.01); *A61M 2205/6063* (2013.01)

(58) Field of Classification Search
CPC ............ A61M 5/3286; A61M 5/31586; A61M 5/31581; A61M 5/5086; A61M 2205/6045; A61M 2205/6036; A61M 2205/6063; A61M 2205/6072; A61M 2205/6081; A61M 2205/6054; A61M 2005/2411; A61M 2005/2403; A61M 2005/2407; A61M 2005/2414; G16H 20/17
USPC .......... 604/152, 187, 189, 211, 224, 232, 67
See application file for complete search history.

(56) References Cited

U.S. PATENT DOCUMENTS

| | | | | |
|---|---|---|---|---|
| 4,592,745 A * | 6/1986 | Rex | ......................... | A61M 5/24 604/152 |
| 4,990,142 A * | 2/1991 | Hoffman | ................. | A61M 5/24 604/232 |
| 6,582,399 B1 | 6/2003 | Smith et al. | | |
| 2005/0209522 A1 * | 9/2005 | Tadokoro | ............. | A61B 5/0245 604/66 |
| 2012/0101446 A1 * | 4/2012 | Heald | ................. | A61M 5/2033 604/189 |
| 2012/0279996 A1 * | 11/2012 | Pappalardo | ......... | A61M 5/2053 222/326 |
| 2013/0274655 A1 | 10/2013 | Jennings et al. | | |
| 2014/0243750 A1 * | 8/2014 | Larsen | ..................... | G01B 7/30 604/218 |
| 2014/0330215 A1 * | 11/2014 | Kikuchi | .................. | A61M 5/24 604/189 |
| 2017/0281857 A1 * | 10/2017 | Wight | ................. | A61M 5/1452 |
| 2018/0353699 A1 | 12/2018 | Helmer et al. | | |
| 2018/0369482 A1 * | 12/2018 | Pedersen | ............. | A61M 5/3146 |

FOREIGN PATENT DOCUMENTS

| | | |
|---|---|---|
| CN | 102413856 A | 4/2012 |
| CN | 102614565 A | 8/2012 |
| CN | 103153366 A | 6/2013 |
| CN | 203263947 U | 11/2013 |
| CN | 103648553 A | 3/2014 |
| CN | 102427841 B | 11/2014 |
| CN | 104174099 A | 12/2014 |
| CN | 104321095 A | 1/2015 |
| CN | 104684603 A | 6/2015 |
| CN | 105339027 A | 2/2016 |
| CN | 206081227 U | 4/2017 |
| CN | 107405448 A | 11/2017 |
| CN | 107614036 A | 1/2018 |
| CN | 108744160 A | 11/2018 |
| CN | 109772823 A | 5/2019 |
| EP | 0897728 B1 | 5/2003 |
| TW | 201521811 A | 6/2015 |
| TW | 201741913 A | 12/2017 |
| TW | 201808366 A | 3/2018 |
| TW | 201831210 A | 9/2018 |
| TW | I670097 B | 9/2019 |
| WO | WO/0187386 A1 | 11/2001 |
| WO | WO-2009125582 A1 * | 10/2009 ............. A61M 5/24 |
| WO | WO2018206494 A1 | 11/2018 |
| WO | WO2019009638 A1 | 10/2019 |

OTHER PUBLICATIONS

English text for WO-2009125582-A1 (Year: 2009).*
https://www.nejs.app/2017/08/ismp-2017-ismp-guidelines-for.html.

* cited by examiner

COMMON INJECTION DEVICE

CROSS-REFERENCE TO RELATED INVENTIONS

This invention patent application is a national stage entry under 35 U.S.C. 371 and claims the benefit of International Invention Application No. PCT/CN2019/106677, filed on Sep. 19, 2019. The entire contents of which are hereby incorporated herein by reference thereto.

BACKGROUND OF THE INVENTION

1. Field of the Invention

The present invention relates to an injection device, and especially a common injection device that can be used to assemble an injection needle containing a drug and provide readable drug information.

2. Description of Related Art

Based on the safety regulations for drug injection, a conventional injection device already has the function of controlling or adjusting the injection dose of drug. That is, the metering type injection device is attached to an injection needle containing a drug. It uses a propulsion mechanism of the conventional injection device to push a piston in a tube of the injection needle to move a certain distance, and then output a predetermined dose of drug through a needle at a front end of the tube.

Although the conventional injection device can provide the function of controlling the injection dose of drug, during the use of the conventional injection device, a user must first confirm whether the drug filled in the injection needle is correct, and then determine the injection dose and injection propulsion stroke according to the needs of different injection objects after confirmation.

However, the conventional injection device only has the functions of assembling the injection needle and injection advance, and does not have the ability to read the information of the drug in the assembled injection needle. It is difficult to assist the user in confirming whether the intended drug for injection is correct, which leads to the concern of insufficient safety during drug injection.

SUMMARY OF THE INVENTION

The technical problem to be solved by the present invention is to provide a common injection device to solve the problem that the conventional injection device cannot read the drug information in the assembled injection needle, cannot confirm whether the drug to be injected is correct, and that dedicated injection devices must be made for the injection needles containing different drugs as the conventional injection device is not of a general type.

The technical solution proposed by the present invention is to provide a common injection device for assembling an injection needle containing a drug, and the common injection device comprises:
  a needle bushing adapted to assemble with the injection needle and having a connecting portion;
  a drug-information providing portion disposed on the needle bushing and being capable of providing readable information corresponding to the drug in the injection needle; and
  an injection propulsion mechanism detachably connected to the connecting portion of the needle bushing and being capable of providing a pushing force for the injection needle to inject the drug.

According to the above-mentioned common injection device, the drug-information providing portion is formed on an outer surface of the needle bushing and the information corresponding to the drug is visually readable.

According to the above-mentioned common injection device, the injection propulsion mechanism is a manual injection propulsion mechanism and has a housing and a screw push rod set, the housing is detachably connected to the connecting portion of the needled bushing, and the screw push rod set is disposed in the housing and inserted into the injection needle via the needle bushing to provide the pushing force to the injection needle.

According to the above-mentioned common injection device, the injection propulsion mechanism is an electric injection propulsion mechanism and comprises:
  a casing having a front end detachably connected to the connecting portion of the needle bushing;
  a screw push rod set disposed in the casing and driven to extend out of the front end of the casing to insert into the injection needle to provide the pushing force;
  an electric motor disposed in the casing and connected to the screw push rod set; and
  a control assembly disposed in the casing and having a control circuit board with a microprocessor and a switch element, the control circuit board electrically connected to the electric motor to determine an operation mode of the electric motor, and the switch element disposed out of the casing to control switching on or off the control circuit board.

According to the above-mentioned common injection device, the drug-information providing portion is disposed in the needle bushing, provides information corresponding to the drug being read electronically, and is connected to an electronic reading module disposed in the injection propulsion mechanism.

According to the above-mentioned common injection device, the injection propulsion mechanism is an electric injection propulsion mechanism and comprises:
  a casing having a front end detachably connected to the connecting portion of the needle bushing;
  a screw push rod set disposed in the casing and driven to extend out of the front end of the casing to insert into the injection needle to provide the pushing force;
  an electric motor disposed in the casing and connected to the screw push rod set; and
  a control assembly disposed in the casing and having a control circuit board with a microprocessor and a switch element, the control circuit board electrically connected to the electric motor to determine an operation mode of the electric motor, and the switch element disposed out of the casing to control switching on or off the control circuit board;
  wherein the electronic reading module is an angular displacement analog module and has an angular displacement drive formed on an outer surface of the connecting portion of the needle bushing and assembled and rotated with the connecting portion of the needle bushing in the casing of the injection propulsion mechanism, the angular displacement drive is set according to the information corresponding to the drug contained in the injection needle to set a contact transmission section of a specific rotation angle, the electronic reading module is disposed in the casing of the injection propulsion mechanism and has a driven wheel and an angular displacement detection element, the driven wheel is rotated by the angular displacement drive to generate an angular displacement of a specific angle, the angular displacement detection element is connected to the driven wheel and is electrically connected to the control circuit board of the control assembly, and the angular displacement detection element outputs a corresponding angular displacement analog information to the control circuit board according to the angular displacement of the driven wheel driven to rotate, and the microprocessor of the control circuit board reads the corresponding angular displacement analog information to determine the kind of the drug and to decide to execute a specific injection propelling action corresponding to the drug.

According to the above-mentioned common injection device, the angular displacement drive has a structure with at least one turning-angle limiting tooth, the angular displacement drive sets the number of the turning-angle limiting teeth according to the information corresponding to the drug contained in the injection needle, the driven wheel of the electronic reading module is a gear that engages the turning-angle limiting teeth, the angular displacement detection element is a potentiometer or a variable resistor and is electrically connected to the control circuit board of the control assembly, a specific rotation angle range is provided as the contact transmission section by the turning-angle limiting teeth, the area on the periphery of the angular displacement drive is a non-contact transmission section, and the angular displacement detection element outputs a corresponding voltage signal to the control circuit board according to the angular displacement of the driven wheel driven to rotate.

According to the above-mentioned common injection device, the contact transmission section of the angular displacement drive has frictional resistance, a specific length is set according to the information corresponding to the drug contained in the injection needle, the driven wheel of the electronic reading module is a friction wheel that is frictionally driven by the angular displacement drive, the angular displacement detection element is a potentiometer or a variable resistor and is electrically connected to the control circuit board of the control assembly, and the angular displacement detection element outputs a corresponding voltage signal to the control circuit board according to the angular displacement of the driven wheel driven to rotate.

According to the above-mentioned common injection device, the injection propulsion mechanism is an electric injection propulsion mechanism and comprises:
  a casing having a front end detachably connected to the connecting portion of the needle bushing;
  a screw push rod set disposed in the casing and driven to extend out of the front end of the casing to insert into the injection needle to provide the pushing force;
  an electric motor disposed in the casing and connected to the screw push rod set; and
  a control assembly disposed in the casing and having a control circuit board with a microprocessor and a switch element, the control circuit board electrically connected to the electric motor to determine an operation mode of the electric motor, and the switch element disposed out of the casing to control switching on or off the control circuit board;
  wherein the electronic reading module is an angular displacement analog module and has a conductive coating or a conductive sticker formed on a specific section of the outer surface of the connecting portion of the needle bushing, the electronic reading module has an angular displacement detection element, the angular displacement detection element has a coil and is electrically connected to the control circuit board of the control assembly, the angular displacement detection element detects a magnetic flux change according to a distance change of the conductive coating or the conductive sticker due to a rotational angular displacement and outputs a corresponding magnetic flux signal to the control circuit board, and the microprocessor of the control circuit board reads the corresponding magnetic flux signal to determine the kind of the drug and to decide to execute a specific injection propelling action corresponding to the drug.

According to the above-mentioned common injection device, the injection propulsion mechanism is an electric injection propulsion mechanism and comprises:
  a casing having a front end detachably connected to the connecting portion of the needle bushing;
  a screw push rod set disposed in the casing and driven to extend out of the front end of the casing to insert into the injection needle to provide the pushing force;
  an electric motor disposed in the casing and connected to the screw push rod set; and
  a control assembly disposed in the casing and having a control circuit board with a microprocessor and a switch element, the control circuit board electrically connected to the electric motor to determine an operation mode of the electric motor, and the switch element disposed out of the casing to control switching on or off the control circuit board;
  wherein the drug-information providing portion provides photoelectric coding digital information and has a light sensing section whose specific light transmission area is set according to the information corresponding to the drug contained in the injection needle, the electronic reading module is a photoelectric coding module, is disposed in the casing of the injection propulsion mechanism and has a light source and a light detection element, the light source and the light detection element are located on two opposite sides of the light sensing section and are electrically connected to the control circuit board of the control assembly, the light detection element senses the transmittance of the light emitted by the light source through the light sensing section and outputs a corresponding voltage signal to the control circuit board, and the microprocessor of the control circuit board determines the kind of drug and decides to perform a specific injection propulsion action corresponding to the drug.

According to the above-mentioned common injection device, the injection propulsion mechanism is an electric injection propulsion mechanism and comprises:
  a casing having a front end detachably connected to the connecting portion of the needle bushing;
  a screw push rod set disposed in the casing and driven to extend out of the front end of the casing to insert into the injection needle to provide the pushing force;
  an electric motor disposed in the casing and connected to the screw push rod set; and
  a control assembly disposed in the casing and having a control circuit board with a microprocessor and a switch element, the control circuit board electrically connected to the electric motor to determine an operation mode of the electric motor, and the switch element disposed out of the casing to control switching on or off the control circuit board;

wherein the drug-information providing portion has a one-dimensional barcode or a two-dimensional barcode set according to the information corresponding to the drug contained in the injection needle, the electronic reading module is disposed in the casing of the injection propulsion mechanism and has a light source and an image scanning element, the light source and the image scanning element are electrically connected to the control circuit board, the light source emits light on the drug-information providing portion, the image scanning element scans the one-dimensional barcode or two-dimensional barcode of the drug-information providing portion, the microprocessor of the control circuit board determines the kind of the drug by information of scanning the one-dimensional barcode or two-dimensional barcode of the drug-information providing portion and decides to perform a specific injection propulsion action corresponding to the drug.

According to the above-mentioned common injection device, the control assembly further has a display screen and a control module with an operating lever, the display screen and the control module are disposed in the casing and are both electrically connected to the control circuit board, and the display screen and the operating lever are exposed out of the casing.

The beneficial effect that can be achieved by the present invention is that the common injection device mainly utilizes a needle bushing with a drug-information providing portion pre-assembled on the injection needle, and the drug-information providing portion provides readable drug information corresponding to the drug contained in the injection needle, allowing the user to first confirm whether the drug filled in the injection needle is correct through the readable drug-information providing portion. After confirming that the drug is correct, the injection propulsion mechanism is used to connect the needle bushing. According to the drug information and the needs of the injected object, the injection dose is determined and the injection propulsion stroke is executed, thereby ensuring the injection safety.

Furthermore, the common injection device of the present invention is only necessary to set the drug information in the needle bushing according to the drugs contained in different injection needles, and pre-install the needle bushing on the corresponding injection needle. In this way, the injection propulsion mechanism can be connected with injection needles containing different drugs, and the injection propulsion mechanism is compatible and reusable. It is not necessary to make a specific or dedicated injection device according to the injection needles containing different drugs, thereby reducing unnecessary waste and reducing cost.

In the common injection device, the drug information providing portion may be a drug information formed on the outer surface of the needle bushing and can be visually read, or the drug information providing portion may be disposed in the needle bushing and can be electronically readable drug information, and is combined with an electronic reading module disposed in the injection propulsion mechanism to provide the information of the drug contained in the injection needle, so that the user can execute a specific injection propulsion stroke according to the drug information.

In the common injection device, when the drug information providing portion is disposed in the needle bushing and can electronically read the drug information, and is combined with an electronic reading module disposed in the injection propulsion mechanism, the injection propulsion mechanism is selected by an electric injection propulsion mechanism. The control circuit board of the control assembly is electrically connected to the electronic reading module, the electronic reading module can read the drug information provided by the drug information providing portion, and the microprocessor of the control circuit board can obtain the output signal according to the electronic reading module, determine the kind of drug and decide to perform a specific propulsion action corresponding to the drug.

DETAILED DESCRIPTION OF PREFERRED EMBODIMENTS

The following describes the technical means adopted by the present invention to achieve the intended purpose of the invention in conjunction with the drawings and the preferred embodiments of the present invention.

Figure 1:
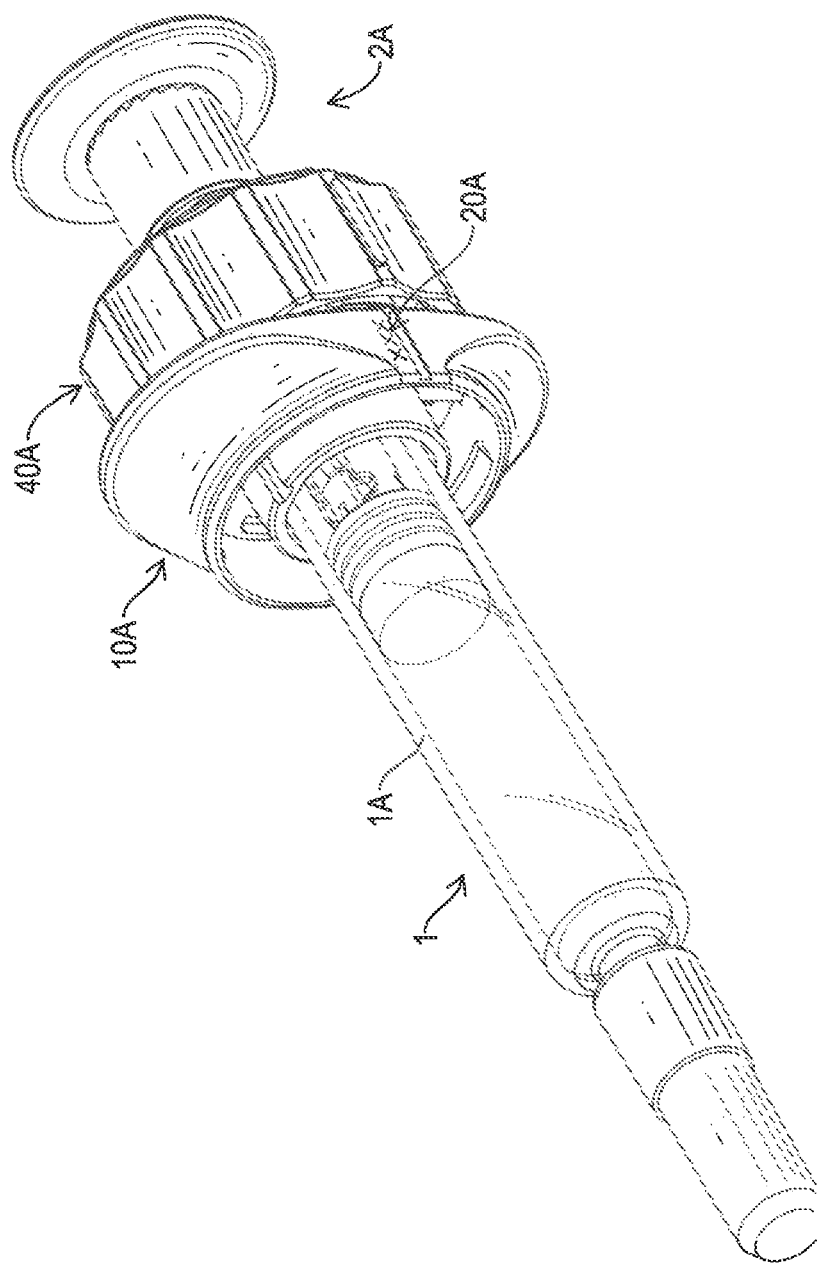
FIG. 1 is a perspective view of a preferred embodiment of a common injection device in accordance with the present invention with a manual injection propulsion mechanism and assembled with an injection needle.
Figure 2:
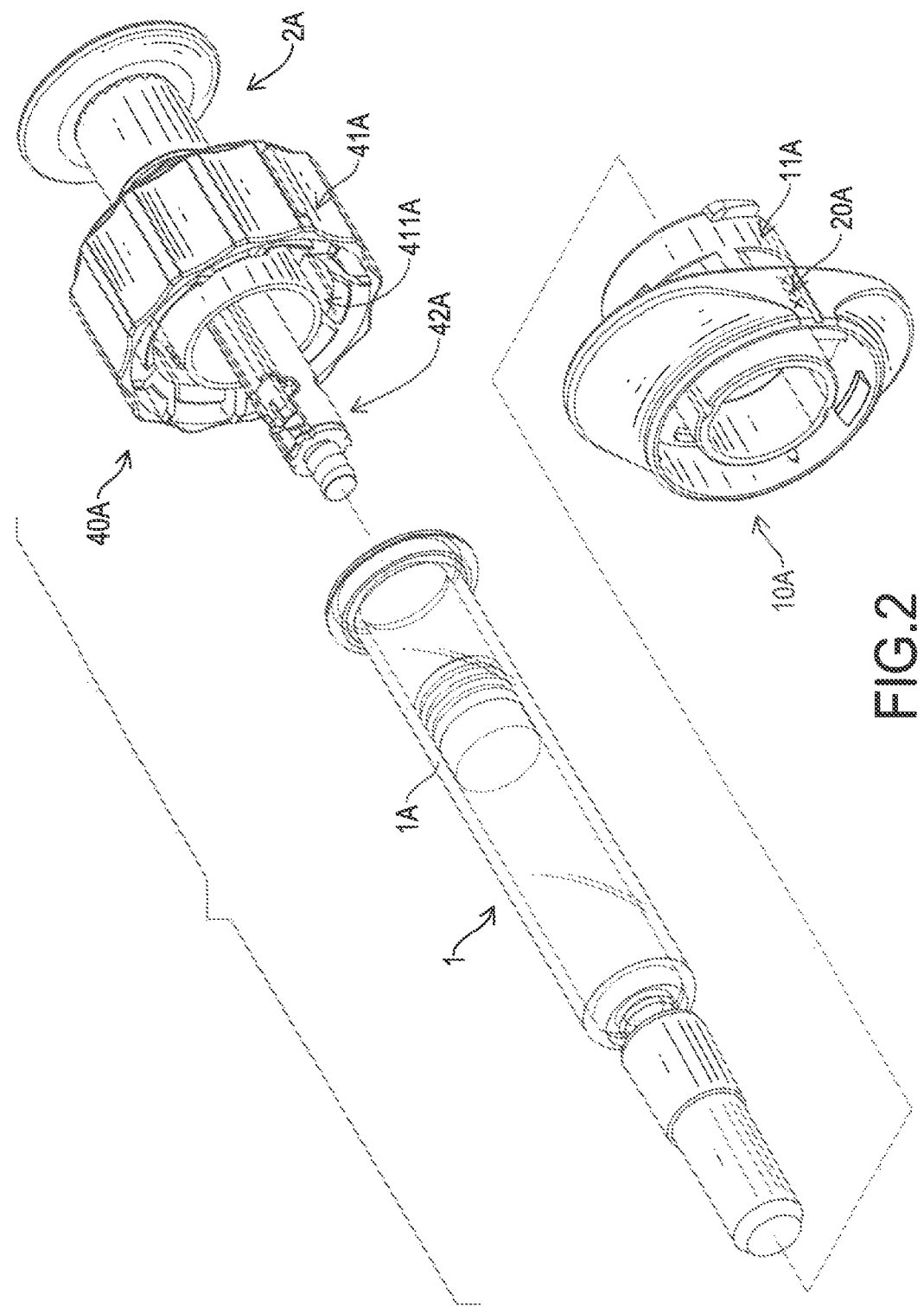
FIG. 2 is a partial exploded perspective view of the common injection device with the manual injection propulsion mechanism and the injection needle in FIG. 1.
Figure 3:
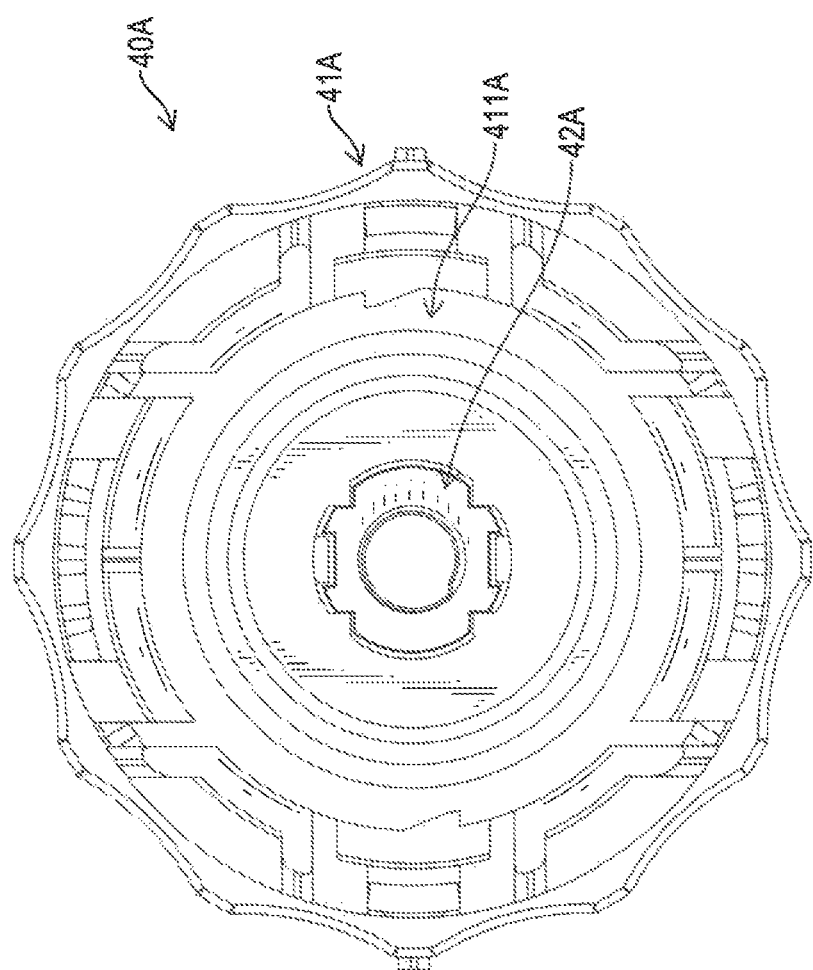
FIG. 3 is a front side view of the manual injection propulsion mechanism in FIGS. 1 to 2.
Figure 4:
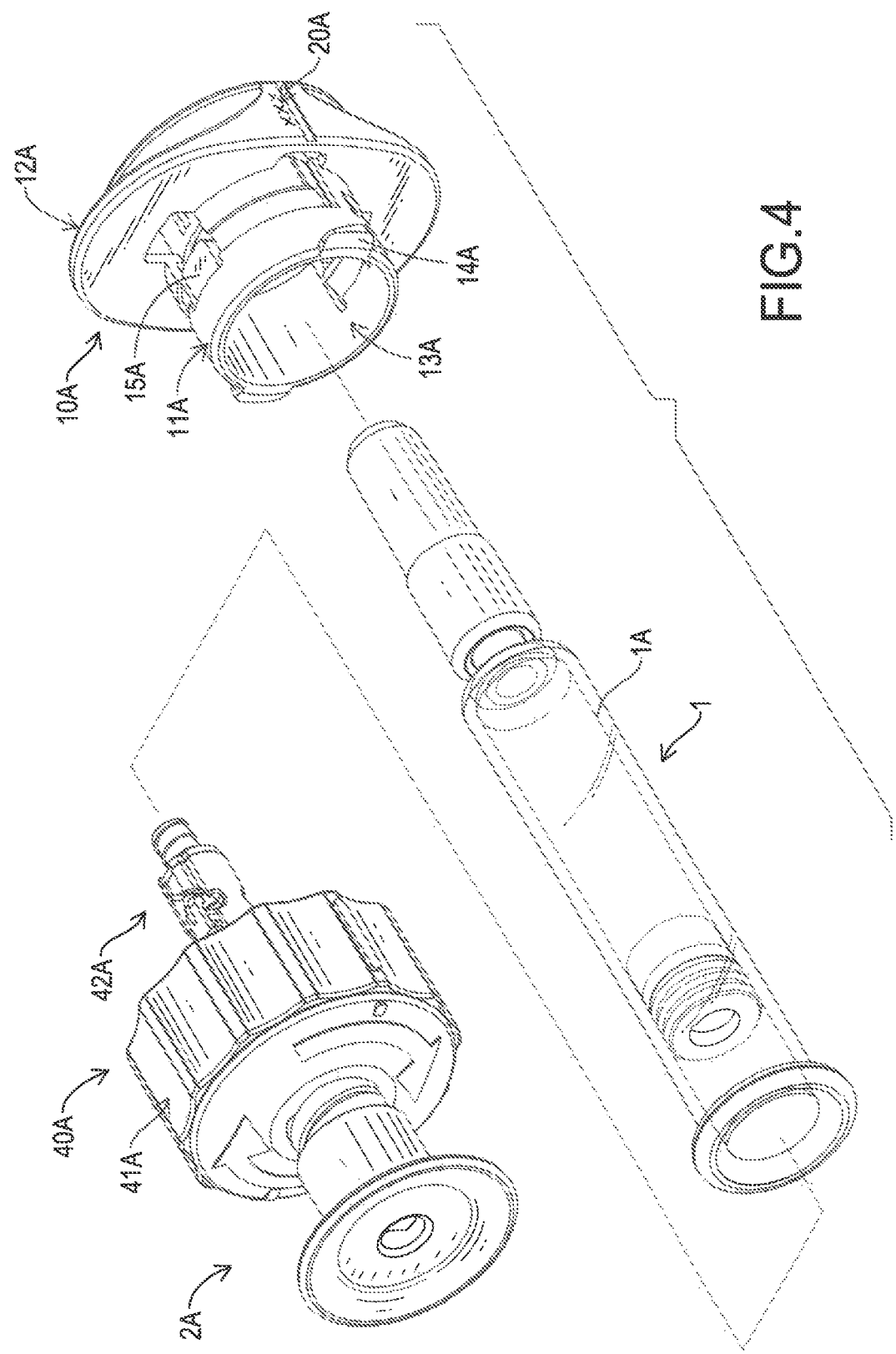
FIG. 4 is another exploded perspective view of the common injection device with the manual injection propulsion mechanism and the injection needle in FIG. 2.
Figure 5:
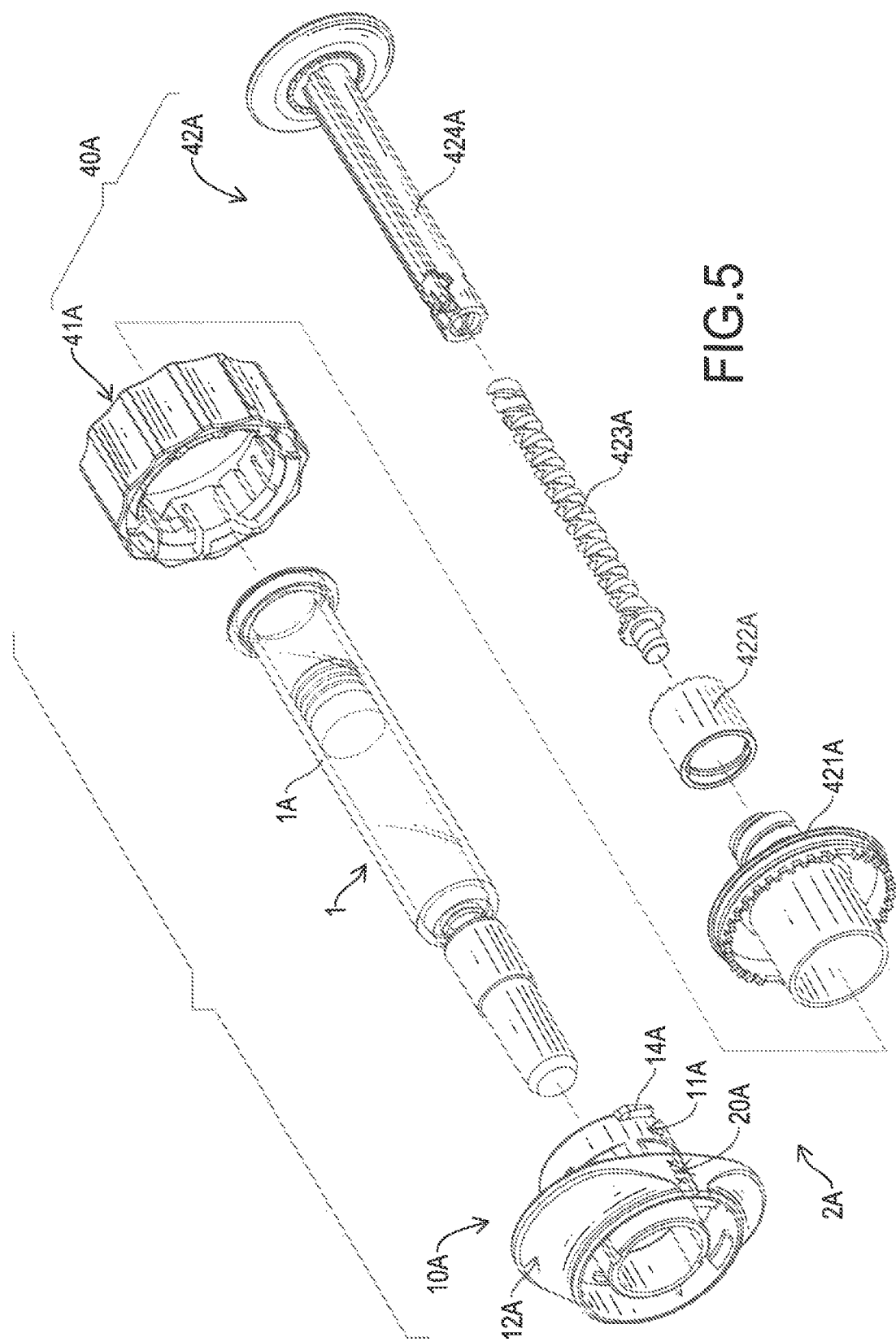
FIG. 5 is a further exploded perspective view of the common injection device with the manual injection propulsion mechanism and the injection needle in FIGS. 1 and 2.
Figure 6:
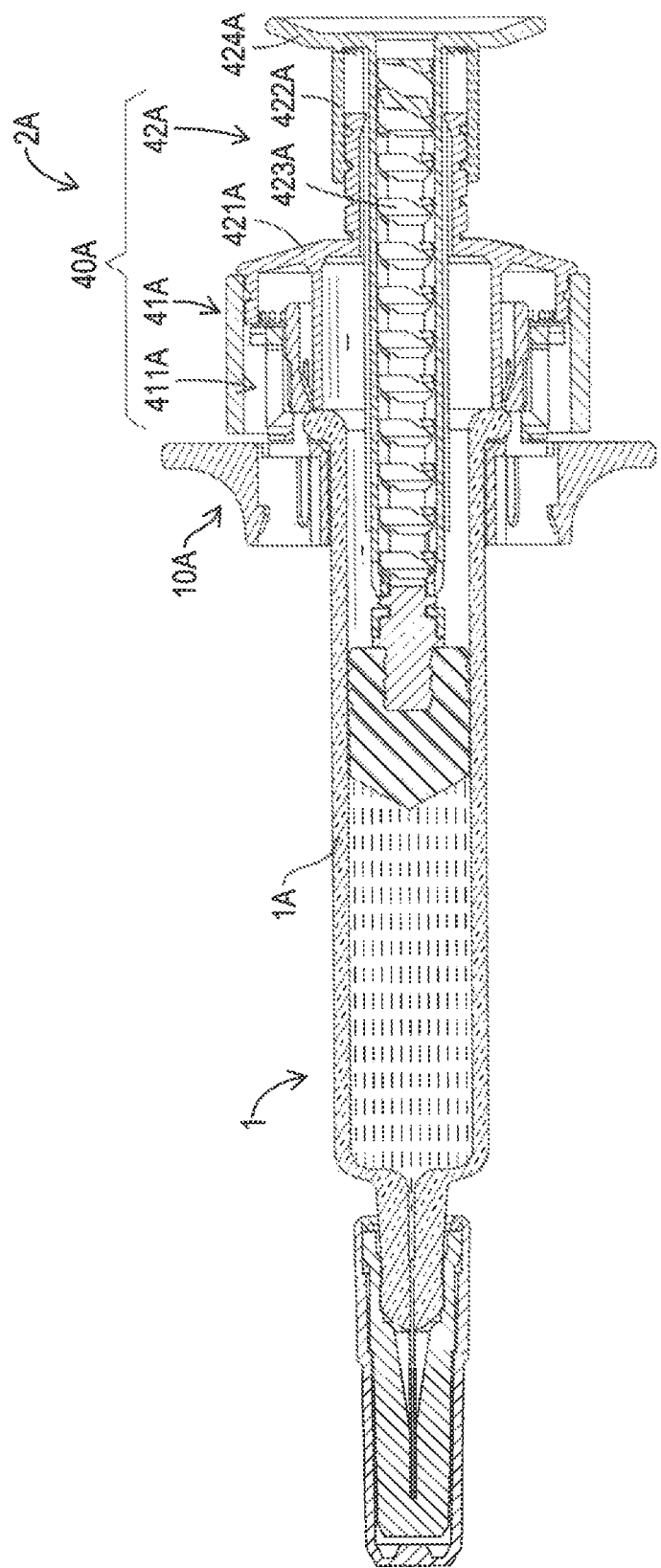
FIG. 6 is a side view in partial section of the common injection device with the manual injection propulsion mechanism and the injection needle in FIG. 1.
Figure 7:
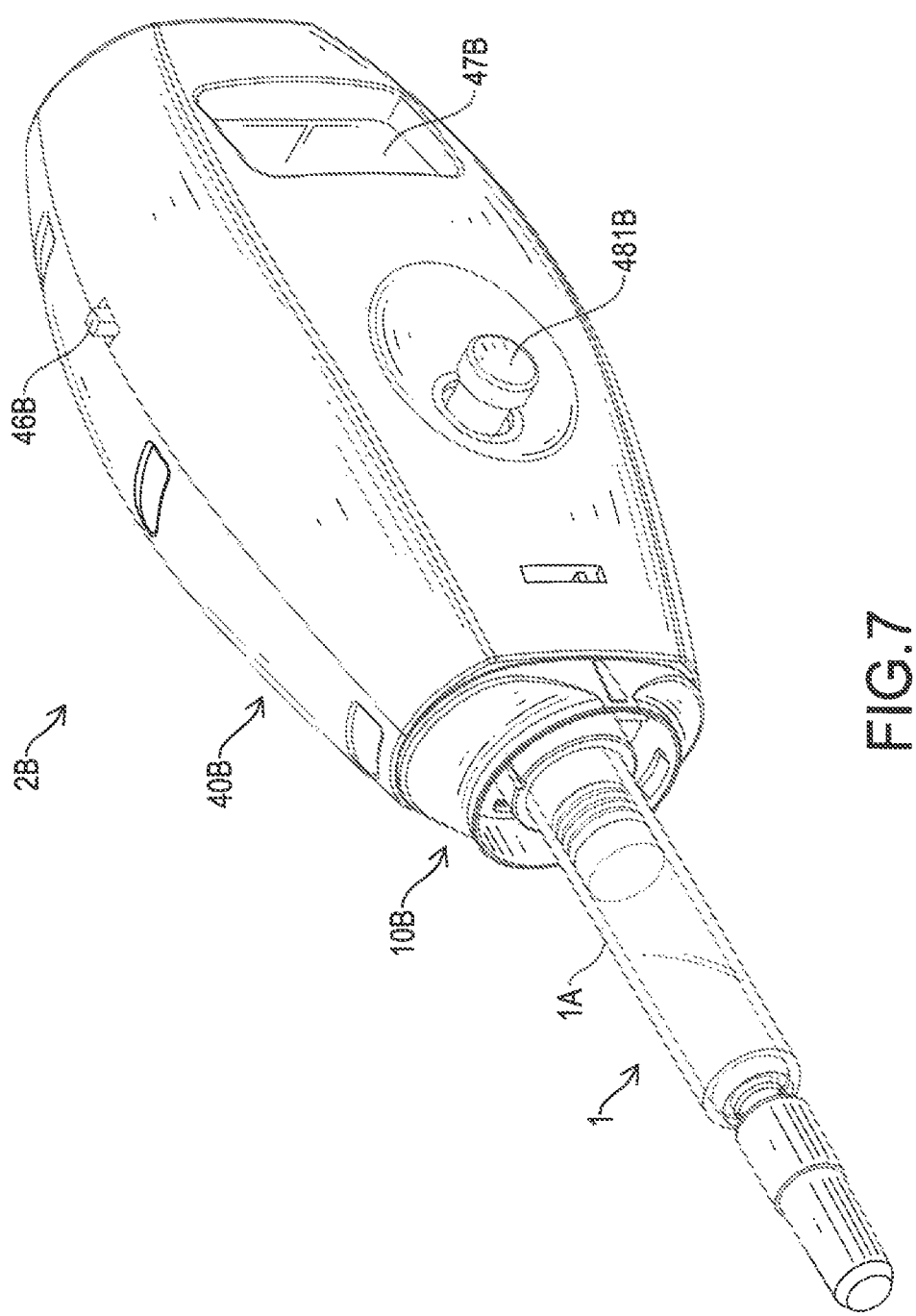
FIG. 7 is a perspective view of a preferred embodiment of a common injection device in accordance with the present invention with an electric injection propulsion mechanism and assembled with an injection needle.
Figure 8:
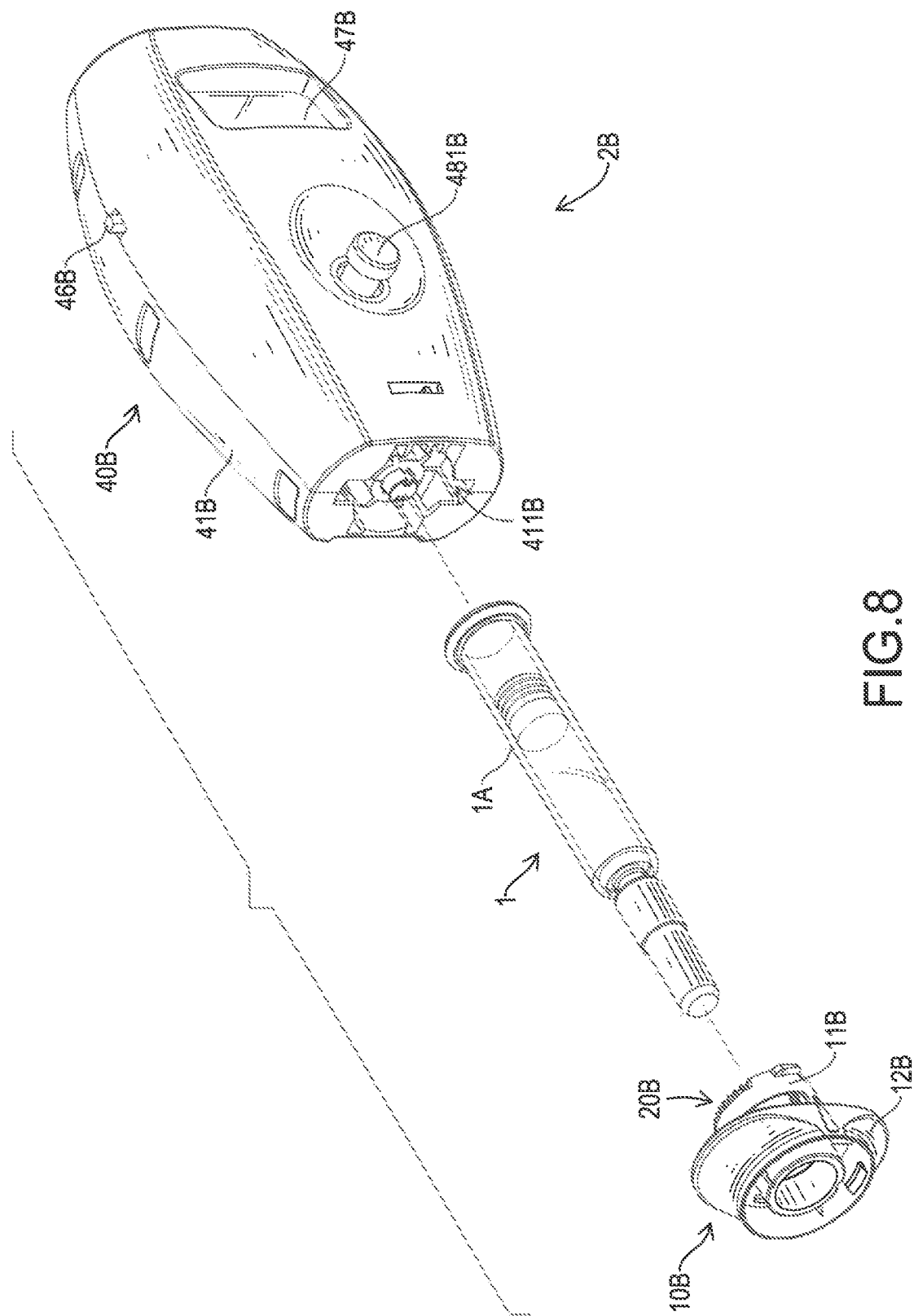
FIG. 8 is a partial exploded perspective view of the common injection device with the electric injection propulsion mechanism and the injection needle in FIG. 7.
Figure 9:
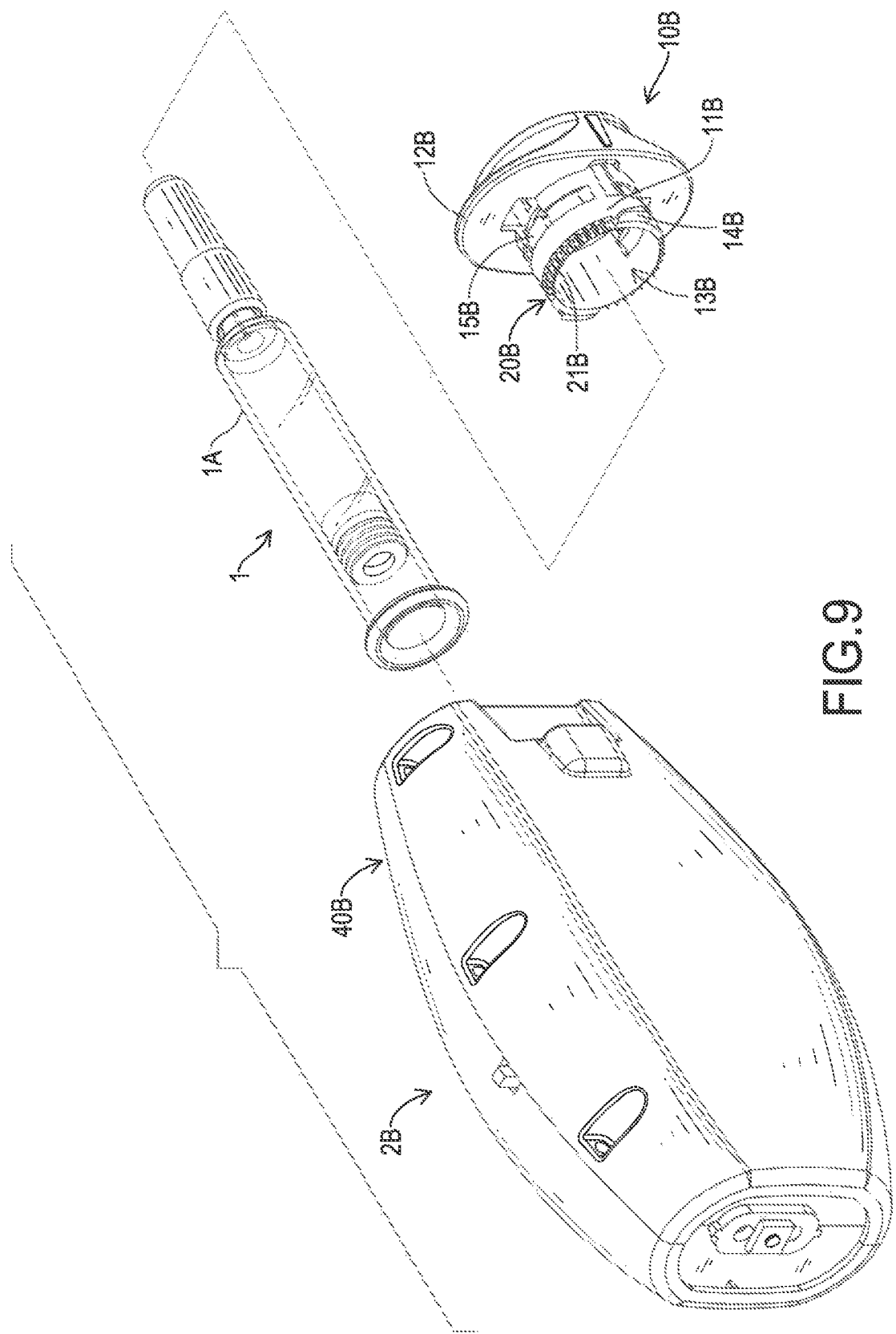
FIG. 9 is another exploded perspective view of the common injection device with the electric injection propulsion mechanism and the injection needle in FIG. 8.
Figure 10:
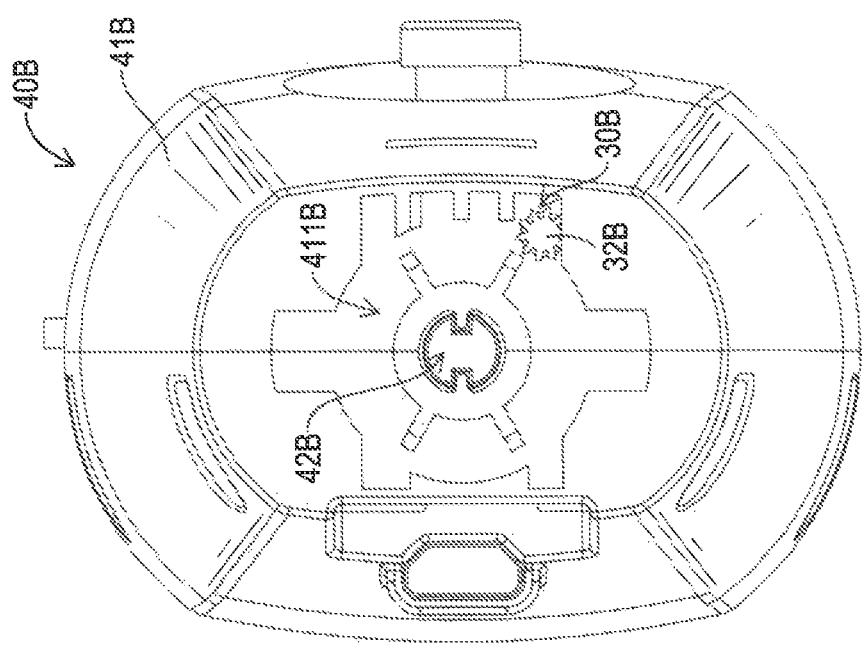
FIG. 10 is a front side view of the electric injection propulsion mechanism in FIG. 8.
Figure 11:
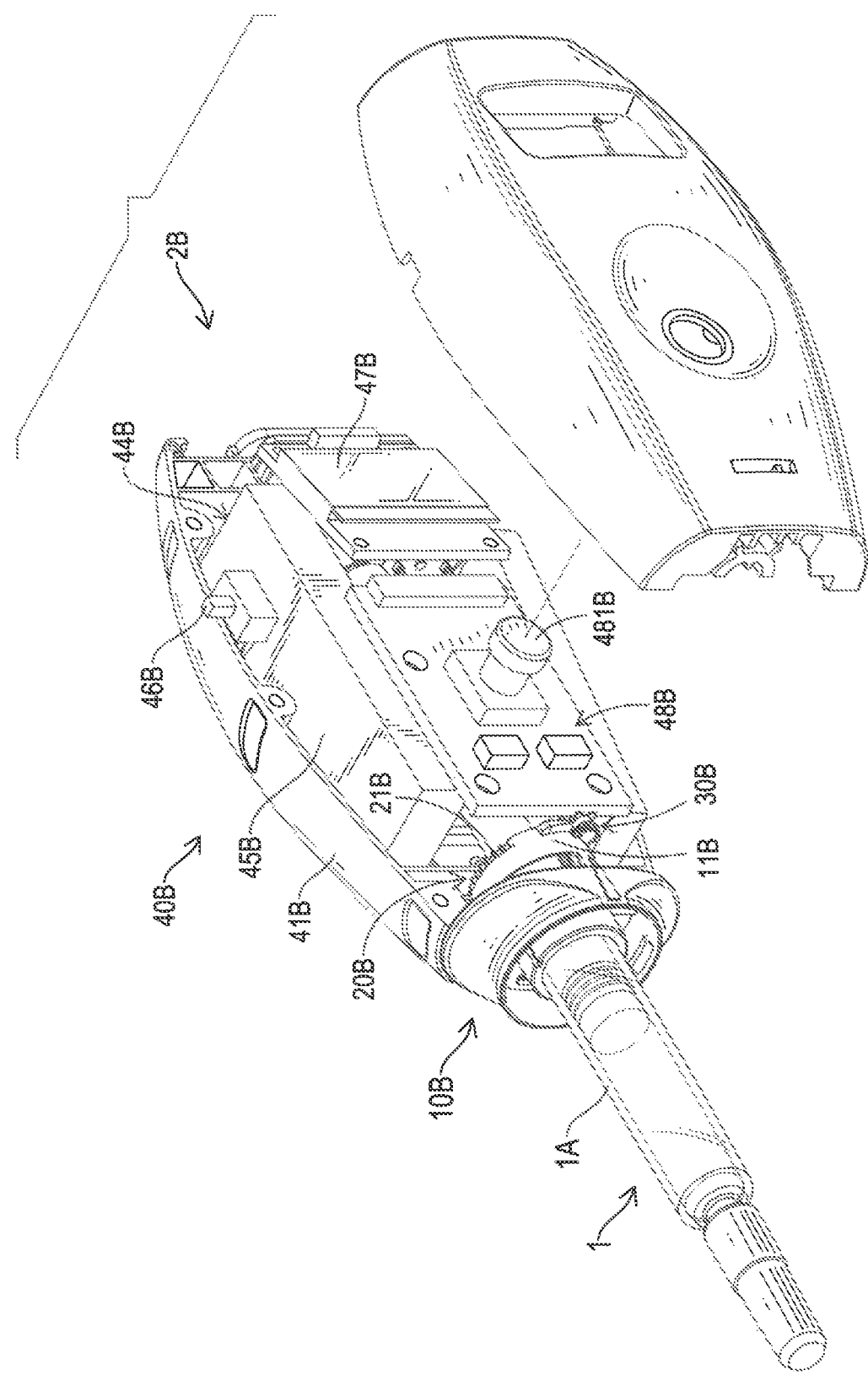
FIG. 11 is a further exploded perspective view of the common injection device with the electric injection propulsion mechanism and the injection needle in FIGS. 7 and 8.
Figure 12:
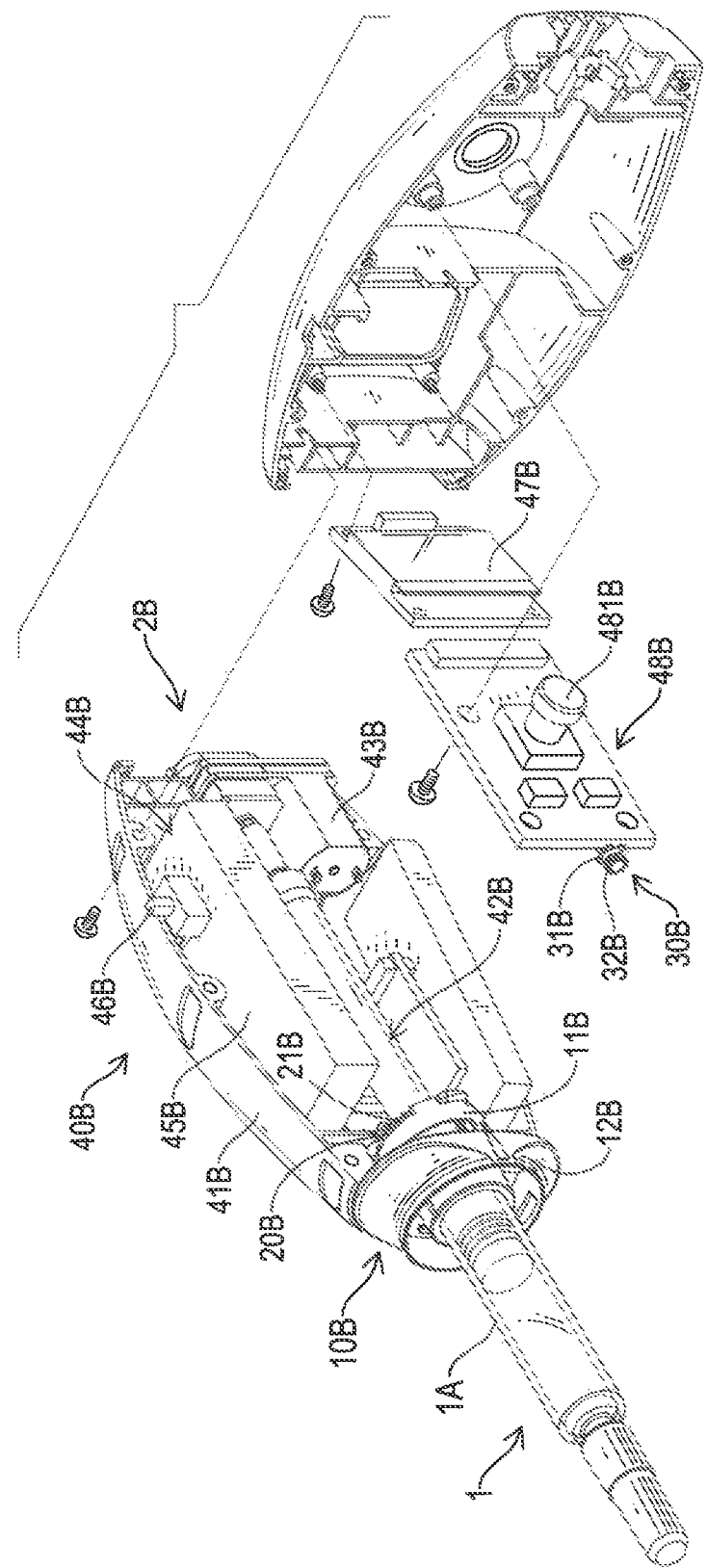
FIG. 12 is another exploded perspective view of the common injection device with the electric injection propulsion mechanism and the injection needle in FIGS. 7 and 8.
Figure 13A:
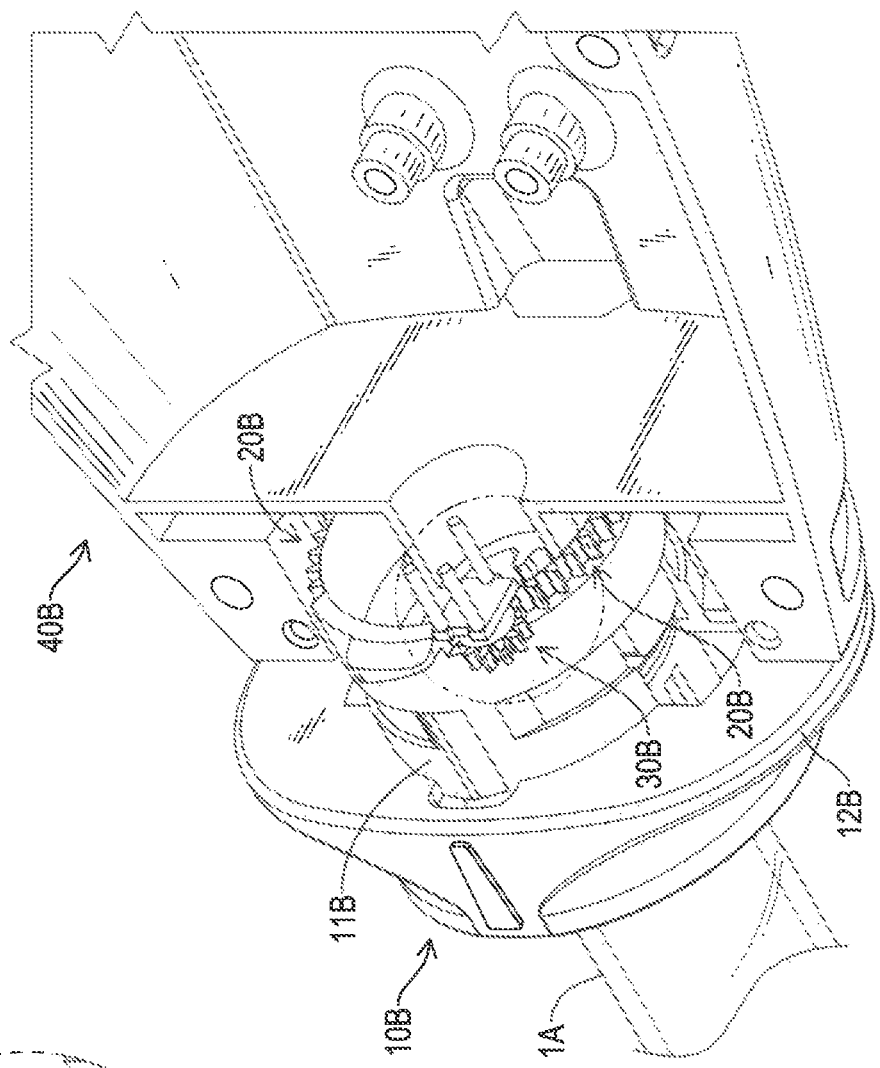
FIGS. 13A and 13B are an enlarged perspective view of the common injection device with the electric injection propulsion mechanism and the injection needle in FIGS. 7, 8, and 12.
Figure 13B:
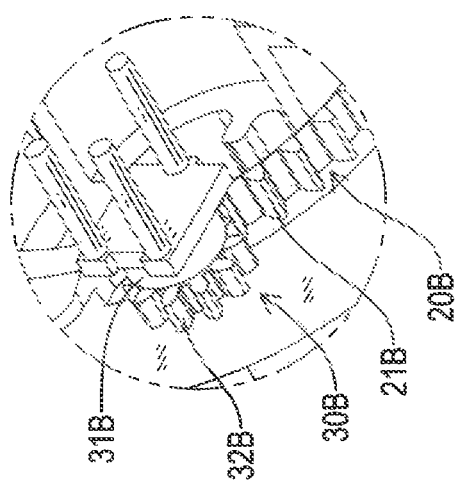
Figure 14:
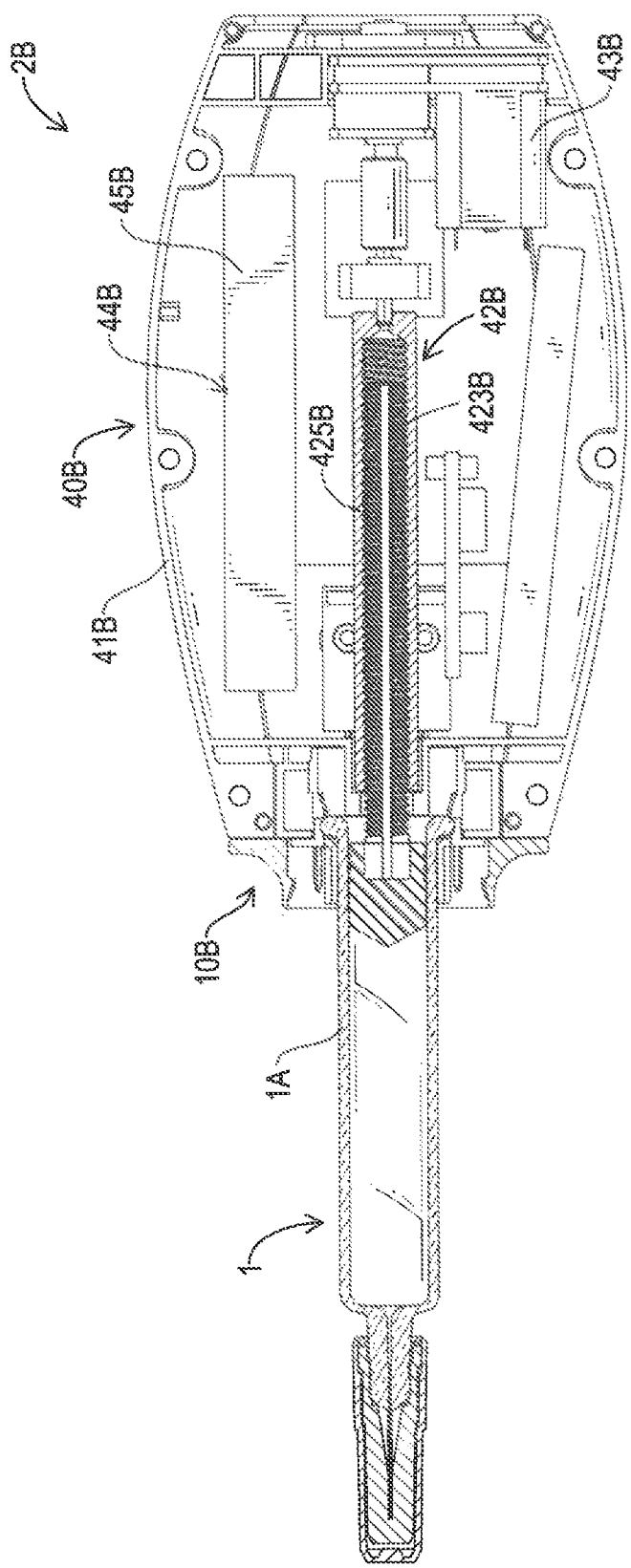
FIG. 14 is a side view in partial section of the common injection device with the electric injection propulsion mechanism and the injection needle in FIG. 7.
Figure 15:
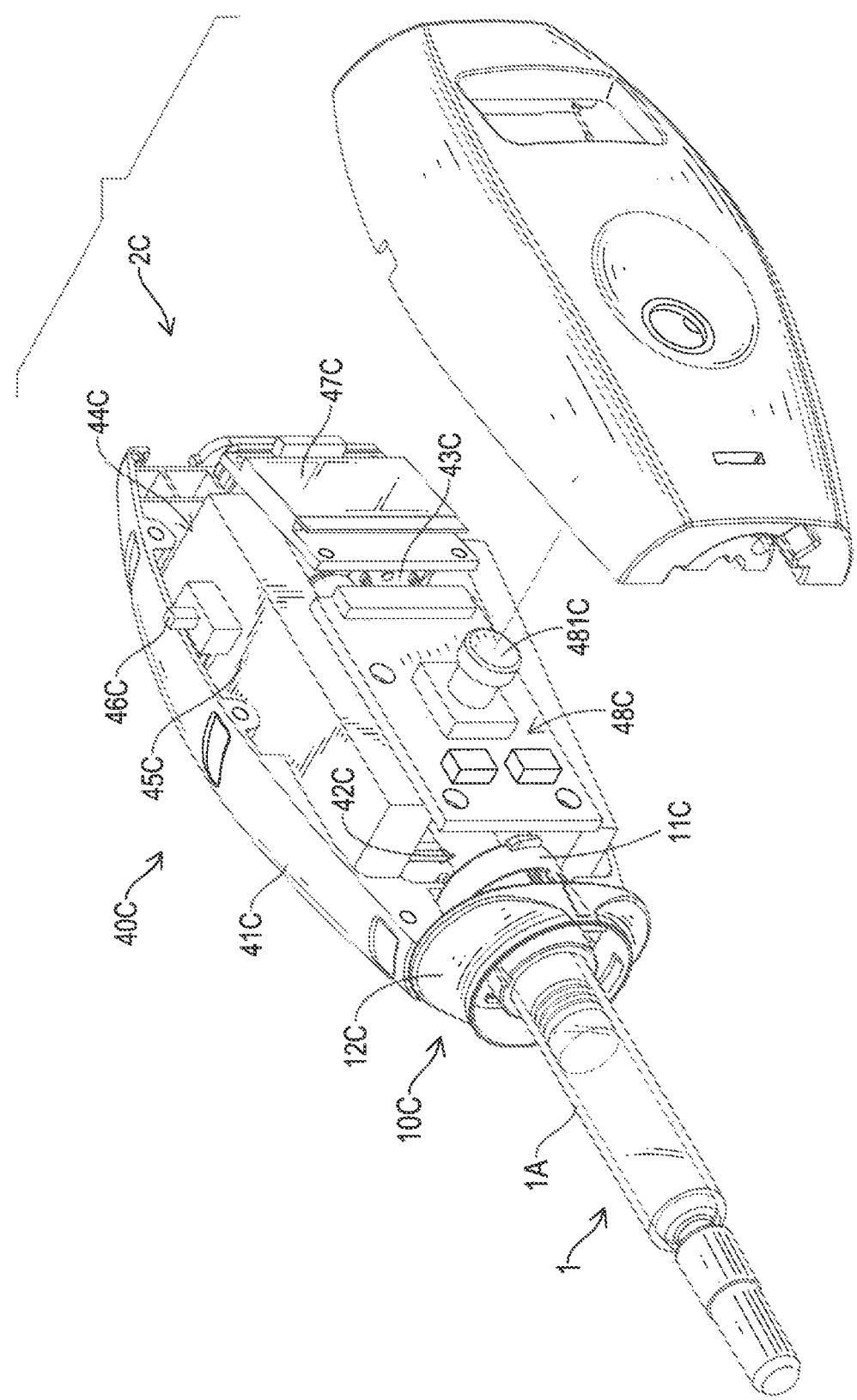
FIG. 15 is an exploded perspective view of a preferred embodiment of a common injection device in accordance with the present invention with an electric injection propulsion mechanism and assembled with an injection needle.
Figure 16:
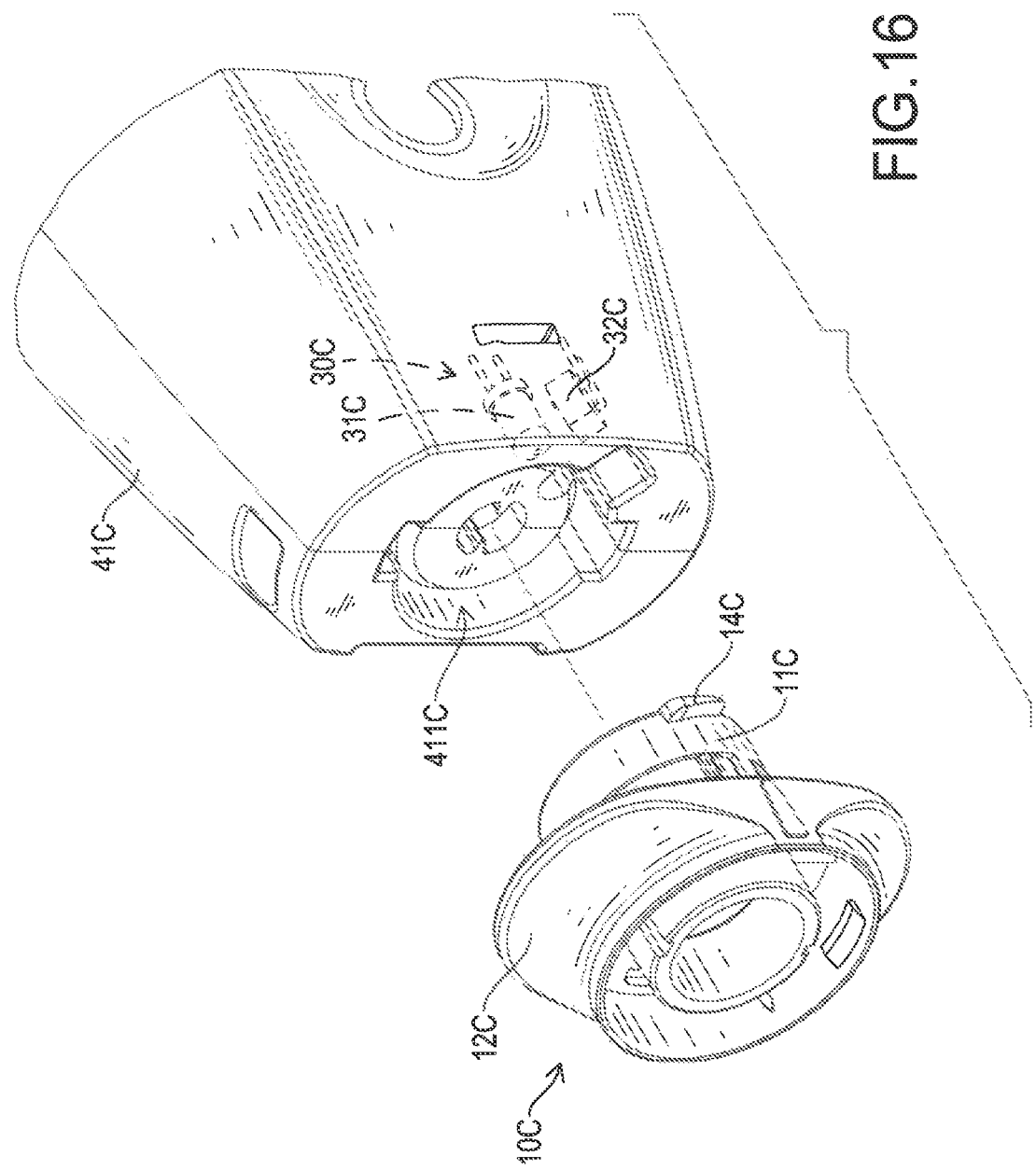
FIG. 16 is a partial exploded perspective view of the common injection device with an electric injection propulsion mechanism in FIG. 15.
Figure 17:
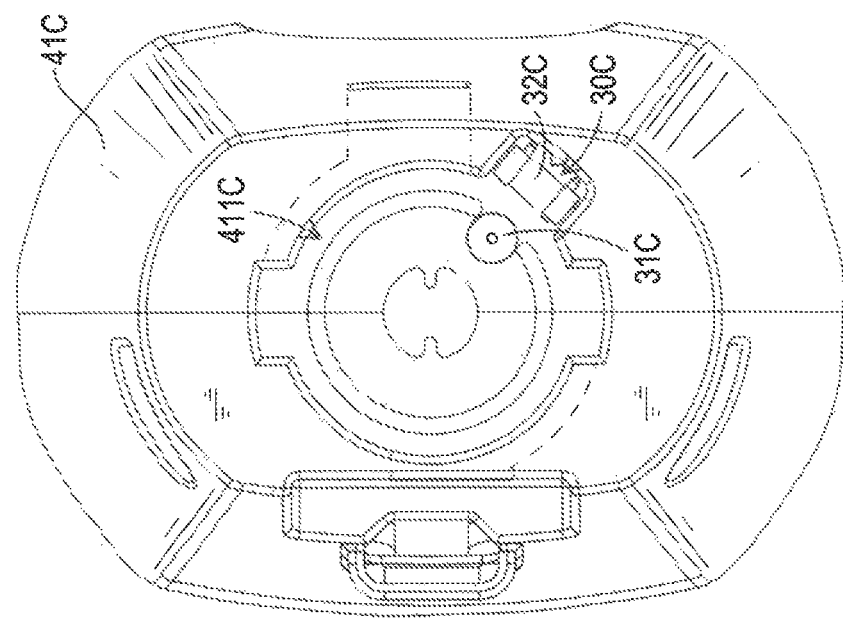
FIG. 17 is a front side view of the electric injection propulsion mechanism in FIG. 15.
Figure 18:
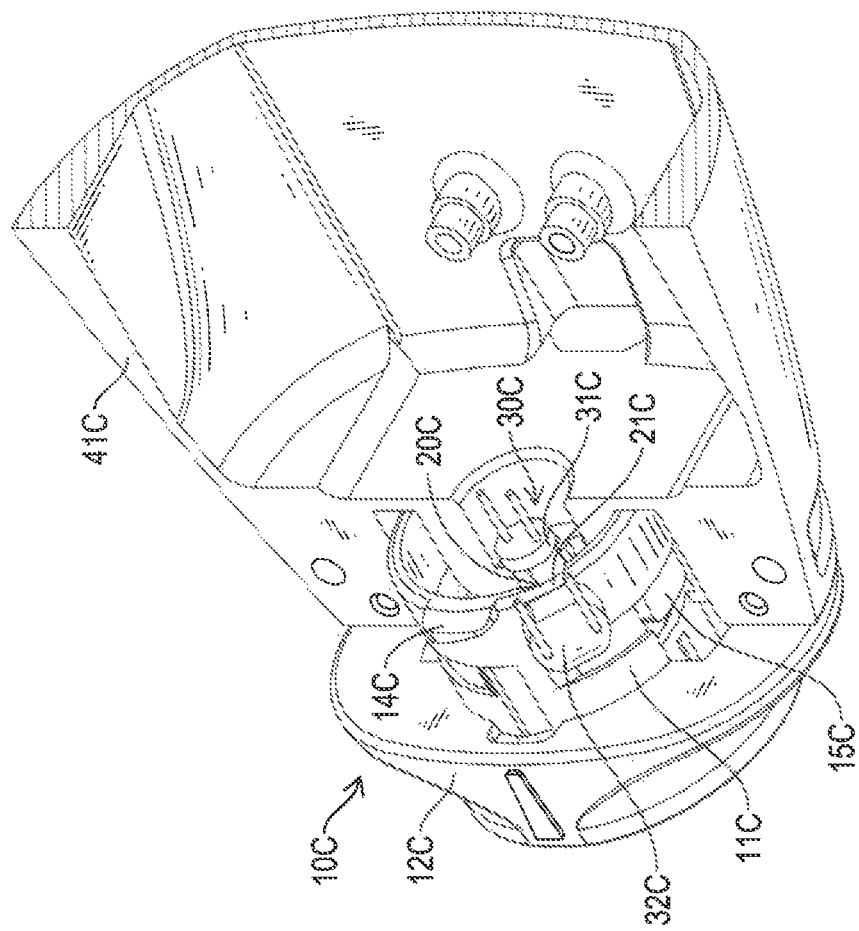
FIG. 18 is another partial perspective view of the common injection device with an electric injection propulsion mechanism in FIG. 15.
Figure 19:
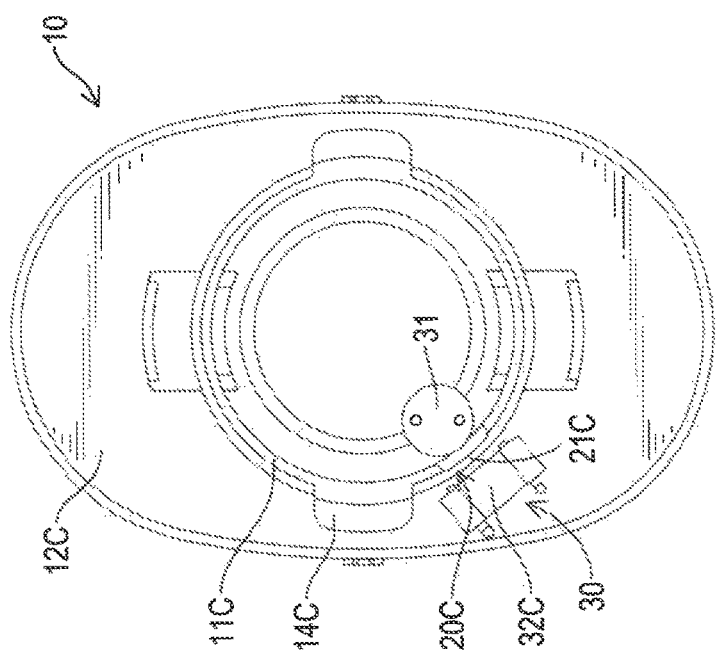
FIG. 19 is a rear side view of a needle bushing and an electronic reading module of the common injection device with an electric injection propulsion mechanism in FIG. 15.common injection device

With reference to FIGS. 1, 7, and 15, preferred embodiments of a common injection device 2A, 2B, 2C of the present invention and an injection needle 1 are disclosed. In the drawings, the injection needle 1 has a tube 1A with a drug contained therein and a piston, a needle is disposed on a front end of the tube 1A, and a needle guard is mounted on an outside of the needle. The common injection device 2A, 2B, 2C of the present invention is assembled on a rear end of the tube 1A of the injection needle 1 and can provide the drug information corresponding to the drug in the injection needle 1, so that a user can perform the corresponding injection action according to the drug information.

With reference to FIGS. 1, 2, 7 to 9, 15, and 16, the common injection device 2A, 2B, 2C may be a manual injection device or an electric injection device, and the common injection device 2A, 2B, 2C includes a needle bushing 10B, 10C, a drug-information providing portion 20A, 20B, 20C, and an injection propulsion mechanism 40A, 40B, 40C.

With reference to FIGS. 2 to 5, 7 to 12, and 15 to 18, the needle bushing 10A, 10B, 10C can be assembled on the rear end of the tube 1A of the injection needle 1, the needle bushing 10A, 10B, 10C has a connecting portion 11A, 11B, 11C, and the connecting portion 11A, 11B, 11C is assembled with the injection propulsion mechanism 40A, 40B, 40C. In each preferred embodiment disclosed in the drawings, the needle bushing 10A, 10B, 10C has a bushing base 12A, 12B, 12C, the bushing base 12A, 12B, 12C is formed on a front end of the connecting portion 11A, 11B, 11C, and the bushing base 12A, 12B, 12C has two operating portions respectively formed on and protruded outwardly from two opposite sides thereof. The needle bushing 10A, 10B, 10C has a middle hole 13A, 13B axially formed through the bushing base 12A, 12B, 12C and the connecting portion 11A, 11B, 11C, and the middle hole 13A, 13B provides the tube 1A of the injection needle 1 to pass through, and the rear end of the tube 1A can be fixed in the middle hole 13A, 13B.

With reference to FIGS. 2 to 5, 7 to 12, and 15 to 18, in each preferred embodiment disclosed in the drawings, the connecting portion 11A, 11B, 11C has multiple engaging protrusions 14A, 14B, 14C formed on an outer peripheral wall thereof and is connected to the injection propulsion mechanisms 40A, 40B, 40C by the multiple engaging protrusions 14A, 14B, 14C. The connecting portion 11A, 11B, 11C of the needle bushing 10A, 10B, 10C has multiple engaging hooks 15A, 15B, 15C formed on and extended into the middle hole 13A, 13B, and the multiple engaging hooks 15A, 15B, 15C can be engaged with and fixed to the rear end of the tube 1A.

With reference to FIGS. 2 to 5, 7 to 12, and 15 to 18, the drug-information providing portion 20A, 20B, 20C is disposed on the needle bushing 10A, 10B, 10C and can provide readable information corresponding to the drug, the drug-information providing portion 20A, 20B, 20C can be one, or the number of the drug-information providing portion 20A, 20B, 20C can be increased according to a combination structure between the assembling portions of the needle bushing 10A, 10B, 10C and the injection propulsion mechanism 40A, 40B, 40C, and is not limited to one drug-information providing portion 20A, 20C.

With reference to FIGS. 1, 2, 4, and 5, the drug-information providing portion 20A can be formed on an outer surface of the needle bushing 10A, and provides information such as patterns, characters, numbers or combinations thereof that can be visually interpreted. Alternatively, as shown in FIGS. 8 to 11 and FIGS. 16 to 19, the drug-information providing portion 20B, 20C can also be disposed in the needle bushing 10B, 10C to provide information that can be read electronically. For example, an electronic reading module 30B, 30C, such as angular displacement analog module or photoelectric encoding module, can read angular displacement analog information or photoelectrically encoded digital information electronically.

With reference to FIGS. 1, 7, and 15, the injection propulsion mechanism 40A, 40B, 40C is detachably assembled on the connecting portion 11A, 11B, 11C of the needle bushing 10A, 10B, 10C and can provide a pushing force to the injection needle 1 for injecting drug. The injection propulsion mechanism 40A, 40C can be a manual or an electric injection propulsion mechanism. With reference to FIGS. 1, 2, 4, and 5, when the drug-information providing portion 20A is information that can be visually read, the injection propulsion mechanism can be a manual injection propulsion mechanism or an electric injection propulsion mechanism. With reference to FIGS. 7 to 9, 15, and 16, when the drug-information providing portion 20B, 20C is information that can be electronically read, the injection propulsion mechanism 40B, 40C is an electric injection propulsion mechanism, and the electronic reading module 30B, 30C is installed in the injection propulsion mechanism 40B, 40C to automatically execute corresponding specific injection actions according to the information of electronic interpretation.

With reference to FIGS. 1 to 6, in the preferred embodiment, the injection propulsion mechanism 40A is a manual injection propulsion mechanism, and the injection propulsion mechanism 40A has a housing 41A and a screw push rod set 42A. The housing 41A is detachably connected to the connecting portion 11A of the needled bushing 10A. In the preferred embodiment, the housing 41A has a connecting recess 411A formed on a front end thereof and at least one locking concave portion communicating with the connecting recess 411A. The connecting portion 11A of the needled bushing 10A that is connected to the rear end of the injection needle 1 can be inserted into the connecting recess 411A and rotated by an angle, the engaging protrusions 14A formed on the outer peripheral wall of the connecting portion 11A engage in the at least one locking concave portion, and the connecting portion 11A of the needle bushing 10A is detachably connected to the front end of the housing 41A.

With reference to FIGS. 1 to 6, the screw push rod set 42A is connected to the housing 41A, and the screw push rod set 42A is inserted into the injection needle 1 via the middle hole 13A of the needle bushing 10A to provide a pushing force to the piston in the tube 1A of the injection needle 1A. The screw push rod set 42A can be selected from various known products and the specific structure thereof will not be repeated here. Alternatively, as the preferred embodiment shown in FIGS. 1 to 6, the screw push rod set 42A includes a connecting element 421A, a mounting ring 422A, a screw push rod 423A, and a pushing rod 424A. The screw push rod 423A is screwed into the pushing rod 424A, the mounting ring 422A is adjusted to screw to a rear end of the connecting element 421A, and is also mounted on an outside of the pushing rod 424A. The screw push rod set 42A and the connecting element 421A are assembled in the housing 41A, the screw push rod 423A and the pushing rod 424A can pass through the connecting element 421A, and the pushing rod 424A can be manually pushed to drive the screw push rod 423A to move forward and extend into the tube 1A of the injection needle 1 to provide a push force to the piston in the tube 1A.

With reference to FIGS. 1 to 6, in the preferred embodiment, the injection propulsion mechanism 40A is a manual injection propulsion mechanism, after the needle bushing 10A that is connected to the rear end of the injection needle 1 is connected to the front end of the housing 41A of the injection propulsion mechanism 40A, a user manually operates the injection propulsion mechanism to execute the injection propulsion stroke corresponding to the drug according to the drug-information providing portion 20A disposed on the outer surface of the needle bushing 10A to provide visually readable drug information corresponding to the drug contained in the injection needle 1.

With reference to FIGS. 7 to 14 and 15 to 19, in the preferred embodiments, the injection propulsion mechanism 40B, 40C is an electric injection propulsion mechanism, the injection propulsion mechanism 40B, 40C has a casing 41B, 41C, a screw push rod set 42B, 42C, an electric motor 43B, 43C, and a control assembly 44B, 44C. The casing 41B, 41C is a hollow shell, and a front end of the casing 41B, 41C is detachably connected to the connecting portion 11B, 11C of the needle bushing 10B, 10C. In the preferred embodiment, the casing 41B, 41C has a connecting recess 411B, 411C formed on a front end thereof and at least one locking concave portion communicating with the connecting recess 411B, 411C. The connecting portion 11B, 11C of the needled bushing 10B, 10C that is connected to the rear end of the injection needle 1 can be inserted into the connecting recess 411B, 411C and rotated by an angle, the engaging protrusions 14B, 14C formed on the outer peripheral wall of the connecting portion 11B, 11C engage in the locking concave portion, and the connecting portion 11B, 11C of the needle bushing 10B, 10C is detachably connected to the front end of the casing 41B, 41C.

With reference to FIGS. 7 to 14 and 15 to 19, the screw push rod set 42B, 42B is connected to the casing 41B, 41C, and is driven to extend out of the front end of the casing 41B, 41C to insert into the tube 1A of the injection needle 1 to push the piston. The screw push rod set 42B, 42C can be selected from various known products and the specific structure thereof will not be repeated here. Alternatively, as the preferred embodiment shown in the drawings, the screw push rod set 42B, 42C includes a screw push rod 423B and a screw guide rod 425B. The screw guide rod 425B is pivotally mounted in the casing 41B, 41C to rotate at a fixed point, and the screw push rod 423B is screwed in the screw guide rod 425B and is driven by the screw guide rod 425B to move forwardly and extend into the tube 1A of the injection needle 1 to push the piston.

With reference to FIGS. 7 to 14 and 15 to 19, the electric motor 43B, 43C is disposed in the casing 41B, 41C and is connected to the screw push rod set 42B, 42C to drive the screw push rod set 42B, 42C to generate a pushing force for the piston to move in a straight line. As the preferred embodiment shown in the drawings, the electric motor 43B, 43C is connected to a rear end of the screw guide rod 425B via a spindle thereof and a coupling element, so as to drive the screw guide rod 425B of the screw push rod set 42B, 42C to rotate, and then the screw push rod 423B is driven by the screw guide rod 425B to extend forward into the tube 1A of the injection needle 1 to push the piston.

With reference to FIGS. 7 to 14 and 15 to 19, the control assembly 44B, 44C is disposed in the casing 41B, 41C, and the control assembly 44B, 44C has a control circuit board 45B, 45C with a microprocessor and a switch element 46B, 46C. The control circuit board 45B, 45C is electrically connected to the electric motor 43B, 43C, and can determine the operation mode of the electric motor 43B, 43C to perform the corresponding injection action. The switch element 46B, 46C is disposed out of the casing 41B, 41C, and can control switching on or off the control circuit board 45B, 45C to activate the electric motor 43B, 43C to drive the screw push rod set 42B, 42C to execute an injection propulsion stroke.

With reference to FIGS. 7 to 14 and 15 to 19, the control assembly 44B, 44C further has a display screen 47B, 47C and a control module 48B, 48C. The display screen 47B, 47C and the control module 48B, 48C are disposed in the casing 41B, 41C, and the control module 48B, 48C and the display screen 47B, 47C are both electrically connected to the control circuit board 45B and 45C. The control module 48B, 48C has an operating lever 481B, 481C. The display screen 47B, 47C and the operating lever 481B, 481C are all exposed out of the casing 41B, 41C, the setting and control of the electric motor 43B, 43C can be performed through the operating lever 481B, 481C and the switch element 46B, 46C of the control module 48B, 48C to drive the screw push rod set 42B, 42C to perform a stable propulsion stroke and switch. The control assembly 44B, 44C can be selected from known products, and its specific structure will not be repeated here.

With reference to FIGS. 7 to 14 and 15 to 19, when the injection propulsion mechanism 40B, 40C is an electric injection propulsion mechanism, the, and the drug-information providing portion 20B, 20C is disposed in the needle bushing 10B, 10C and provides information that is electronically readable. The drug-information providing portion 20B, 20C is connected to an electronic reading module 30B, 30C, the electronic reading module 30B, 30C is disposed in the casing 41B, 41C of the injection propulsion mechanism 40B, and the electronic reading module 30B, 30C is electrically connected to the control circuit board 45B, 45C to read the electronically readable drug information provided by the drug-information providing portion 20B, 20C. The control circuit board 45B, 45C determines the operation mode of driving the electric motor 43B, 43C according to the electronically read drug information to execute a corresponding specific injection propulsion stroke.

In the above, when the drug-information providing portion 20B, 20C provides drug information that is electronically readable, the drug-information providing portion 20B, 20C and a matching electronic reading module 30B, 30C can be implemented by at least the following preferred embodiments.

With reference to FIGS. 7 to 14, in the preferred embodiment, the drug-information providing portion 20B provides angular displacement analog information. When the electronic reading module 30B is an angular displacement analog module, the drug-information providing portion 20B has an angular displacement drive 21B formed on an outer surface of the connecting portion 11B of the needle bushing 10B and can be assembled and rotated with the connecting portion 11B of the needle bushing 10B in the casing 41B of the injection propulsion mechanism 40B. The angular displacement drive 21B is set according to the information of the drug filled in the injection needle 1 to set its contact transmission section of a specific rotation angle. The electronic reading module 30B is disposed in the casing 41B of the injection propulsion mechanism 40B, and the electronic reading module 30B includes a driven wheel 32B and an angular displacement detection element 31B. The driven wheel 32B can be rotated by the angular displacement drive 21B to generate an angular displacement of a specific angle. The angular displacement detection element 31B is connected to the driven wheel 32B and is electrically connected to the control circuit board 45B of the control assembly 44B. The angular displacement detection element 31B outputs a corresponding angular displacement analog information to the control circuit board 45B according to the angular displacement of the driven wheel 32B driven to rotate.

With reference to FIGS. 7 to 14, in the preferred embodiment, the angular displacement drive 21B may have a structure with one turning-angle limiting tooth or multiple continuous of turning-angle limiting teeth. The angular displacement drive 21B sets the number of the turning-angle limiting teeth according to the information of the drug contained in the injection needle 1. For example, according to drug A, the angular displacement drive 21B is set to have one turning-angle limiting tooth, and according to drug B, the angular displacement drive 21B is set to have two continuous turning-angle limiting teeth, etc. The driven wheel 32B of the electronic reading module 30B is capable of a gear that engages the turning-angle limiting teeth, the angular displacement detection element 31B can be a potentiometer or a variable resistor. A specific rotation angle range is provided as a contact transmission section by the turning-angle limiting teeth, the area on the periphery of the angular displacement drive 21B is the non-contact transmission section, and the non-contact transmission section is a section that cannot drive the driven wheel 32B to rotate. The angular displacement detection element 31B outputs a corresponding voltage signal to the control circuit board 45B according to the angular displacement of the driven wheel 32B driven to rotate.

As described above, since the number of teeth of the turning-angle limiting teeth of the angular displacement drive 21B is small, the amount of angular displacement generated by the driven wheel 32B is small, the number of teeth of the turning-angle limiting teeth of the angular displacement drive 21B is large, and the amount of the angular displacement generated by the driven wheel 32B is large. The angular displacement detection element 31B generates voltage signals of different magnitudes according to the change of the rotational angular displacement of the driven wheel 32B. According to the linear relationship, the microprocessor of the control circuit board 45B can read the generated voltage signals in a specific interval to determine the kind of drug and to decide to execute a specific injection propelling action corresponding to the drug.

Similarly, the angular displacement drive 21B can be changed to a contact transmission section with frictional resistance, and a specific length can be set according to the information of the drug filled in the injection needle 1, and the driven wheel 32B of the electronic reading module 30B can be changed to a friction wheel or the like that is frictionally driven by the angular displacement drive 21B. That is, the friction transmission structure is used instead of the gear transmission structure, and can also achieve the same function as the above.

Furthermore, the drug-information providing portion 20B provides angular displacement analog information. When the electronic reading module is an angular displacement analog module, the drug-information providing portion 20B has a conductive coating or a conductive sticker formed on a specific section of the outer surface of the connecting portion 11B of the needle bushing 10B, and the electronic reading module 30B is disposed in the casing 41B of the injection propulsion mechanism 40B. The electronic reading module includes an angular displacement detection element 31B, and the angular displacement detection element 31B has a coil and is electrically connected to the control circuit board 45B of the control assembly 44B. The angular displacement detection element 31B detects its magnetic flux change according to a distance change of the conductive coating or the conductive sticker due to a rotational angular displacement, and outputs a corresponding magnetic flux signal to the control circuit board 45B (not shown).

With reference to FIGS. 15 to 19, in the preferred embodiment, the drug-information providing portion 20C provides photoelectric coding digital information. When the electronic reading module 30C is a photoelectric coding module, the drug-information providing portion 20C has a light sensing section 21C whose specific light transmission area is set according to the information of drug filled in the injection needle 1. When the needle bushing 10C is made of a completely opaque material, the drug-information providing portion 20C is formed in a local opening in a predetermined sensing area of the connecting portion 11C of the needle bushing 10C. The size of hole area or light-shielding pattern of the local opening is set according to information of different drugs, so as to provide the light sensing section 21C with a specific light transmitting area. Alternatively, a predetermined sensing area of the connecting portion 11C of the needle bushing 10C is formed with a full aperture, and the drug-information providing portion 20C is disposed in a light-shielding layer with a light-shielding coating with a specific pattern in the predetermined sensing area, so as to provide a light sensing section 21C with a specific light-transmitting area.

With reference to FIGS. 15 to 19, the electronic reading module 30C is disposed in the casing 41C of the injection propulsion mechanism 40C. When the connecting portion 11C of the needle bushing 10C is assembled in the casing 41C of the injection propulsion mechanism 40C, a position of the electronic reading module 30C corresponds to a position of the drug-information providing portion 20C. The electronic reading module 30C includes a light source 31C and a light detection element 32C, and the light source 31C and the light detection element 32C can be located on two opposite sides of the light sensing section 21C (That is, the inner and outer sides of the connecting portion 11C of the needle bushing 10C correspond to a position of the light sensing section 21C. The light source 31C and the light detection element 32C are both electrically connected to the control circuit board 45C, and the light detection element 32C can sense the transmittance of the light emitted by the light source 31C through the light sensing section 21C and output a corresponding voltage signal to the control circuit board 45C. The microprocessor of the control circuit board 45C determines the kind of drug and decides to perform a specific injection propulsion action corresponding to the drug.

Additionally, the drug-information providing portion 20C may also be a one-dimensional barcode or a two-dimensional barcode set according to the information of drug filled in the injection needle 1. Preferably, the two-dimensional barcode can be selected as a quick response matrix code (Quick Response Code; QR Code), and the electronic reading module 30C is disposed in the casing 41C of the injection propulsion mechanism 40C, and includes a light source 31C and an image scanning element. The light source 31C and the image scanning element are both electrically connected to the control circuit board 45C. The aforementioned one-dimensional barcode or two-dimensional barcode, light source 31C, and image scanning element for scanning the barcodes are all existing products, and their specific structures will not be repeated here.

When the connecting portion 11C of the needle bushing 10C is assembled in the casing 41C of the injection propulsion mechanism 40C, a position of the electronic reading module 30C corresponds to a position of the drug-information providing portion 20C. The drug-information providing portion 20C is illuminated by the light source, and the image scanning element scans one-dimensional barcode or two-dimensional barcode of the drug-information providing portion 20C, and the microprocessor of the control circuit board 45C determines the kind of drug according to the information generated by scanning the one-dimensional barcode or two-dimensional barcode provided by the drug-information providing portion 20C, and decides to perform a specific injection propulsion action corresponding to the drug.

According to the foregoing description, the common injection device of the present invention is constructed by a combination of a needle bushing 10A, 10C, a drug-information providing portion 20A, 20B, 20C disposed in the needle bushing 10A, 10B, 10C and an injection propulsion mechanism 40A, 40B, detachably connected to the needle bushing 10A, 10B, 10C. The needle bushing 10A, 10B, 10C with the drug-information providing portion 20A, 20B, is pre-installed on the injection needle 1that is contained a drug, and the drug-information providing portion 20A, 20B, 20C provides a readable drug information corresponding to the drug. So a user can confirm that the drug is correct via the readable drug-information providing portion 20A, 20B, 20C, and then connect the needle bushing 10A, 10B, 10C with the injection propulsion mechanism 40A, 40B, 40C, and perform the injection action according to the drug information to ensure the safety of injection. On the other hand, using the combined structure of the injection propulsion mechanism 40A, 40B, 40C to detachably connect the needle bushing 10A, 10B, 10C preset on the injection needle 1, the injection propulsion mechanism 40A, 40B, 40C can be compatible and reused, and it is not necessary to make a specific or dedicated injection device according to the injection needles 1 equipped with different drugs, thereby reducing unnecessary waste and reducing cost.

The above are only the preferred embodiments of the present invention and do not limit the present invention in any form. Although the present invention has been disclosed as above in the preferred embodiments, it is not intended to limit the present invention. Anyone familiar with the professional technology, without departing from the scope of the technical solution of the present invention, can make use of the technical content disclosed above to make slight changes or modification into equivalent embodiments with equivalent changes, but any content that does not depart from the technical solution of the present invention is based on the present invention. Any simple modifications, equivalent changes and modifications made to the above embodiments by technical essence still fall within the scope of the technical solutions of the present invention.

What is claimed is:

1. A common injection device, adapted to assemble with an injection needle containing a drug, characterized in that the common injection device includes:
   a needle bushing adapted to assemble with the injection needle and having
      a connecting portion;
      a bushing base formed on a front end of the connecting portion and having two operating portions respectively formed on and protruded outwardly from two opposite sides thereof; and
      a middle hole axially formed through the bushing base and the connecting portion,
      wherein the connecting portion has multiple engaging hooks formed on and extended into the middle hole, the middle hole enables a tube of the injection needle to pass through, and a rear end of the tube is fixed in the middle hole by the multiple engaging hooks;
   a drug-information providing portion disposed on the needle bushing and being capable of providing readable information corresponding to the drug in the injection needle; and
   an injection propulsion mechanism detachably connected to the connecting portion of the needle bushing and being capable of providing a pushing force for the injection needle to inject the drug.

2. The common injection device as claimed in claim 1, characterized in that the drug-information providing portion is formed on an outer surface of the needle bushing and provides visually readable information corresponding to the drug.

3. The common injection device as claimed in claim 2, characterized in that the injection propulsion mechanism is a manual injection propulsion mechanism and has a housing and a screw push rod set, the housing is detachably connected to the connecting portion of the needled bushing, and the screw push rod set is disposed in the housing and inserted into the injection needle via the needle bushing to provide the pushing force to the injection needle.

4. The common injection device as claimed in claim 2, characterized in that the injection propulsion mechanism is an electric injection propulsion mechanism and comprises:
   a casing having a front end detachably connected to the connecting portion of the needle bushing;
   a screw push rod set disposed in the casing and driven to extend out of the front end of the casing to insert into the injection needle to provide the pushing force;
   an electric motor disposed in the casing and connected to the screw push rod set; and
   a control assembly disposed in the casing and having a control circuit board with a microprocessor and a switch element, the control circuit board electrically connected to the electric motor to determine an operation mode of the electric motor, and the switch element disposed out of the casing to control switching on or off the control circuit board.

5. The common injection device as claimed in claim 1, characterized in that the drug-information providing portion is disposed in the needle bushing, provides information corresponding to the drug being read electronically, and is connected to an electronic reading module disposed in the injection propulsion mechanism.

6. The common injection device as claimed in claim 5, characterized in that the injection propulsion mechanism is an electric injection propulsion mechanism and comprises:

a casing having a front end detachably connected to the connecting portion of the needle bushing;

a screw push rod set disposed in the casing and driven to extend out of the front end of the casing to insert into the injection needle to provide the pushing force;

an electric motor disposed in the casing and connected to the screw push rod set; and a control assembly disposed in the casing and having a control circuit board with a microprocessor and a switch element, the control circuit board electrically connected to the electric motor to determine an operation mode of the electric motor, and the switch element disposed out of the casing to control switching on or off the control circuit board;

wherein the electronic reading module is an angular displacement analog module and has an angular displacement drive formed on an outer surface of the connecting portion of the needle bushing and assembled and rotated with the connecting portion of the needle bushing in the casing of the injection propulsion mechanism, the angular displacement drive is set according to the information corresponding to the drug contained in the injection needle to set a contact transmission section of a specific rotation angle, the electronic reading module is disposed in the casing of the injection propulsion mechanism and has a driven wheel and an angular displacement detection element, the driven wheel is rotated by the angular displacement drive to generate an angular displacement of a specific angle, the angular displacement detection element is connected to the driven wheel and is electrically connected to the control circuit board of the control assembly, and the angular displacement detection element outputs a corresponding angular displacement analog information to the control circuit board according to the angular displacement of the driven wheel driven to rotate, and the microprocessor of the control circuit board reads the corresponding angular displacement analog information to determine the kind of the drug and to decide to execute a specific injection propelling action corresponding to the drug.

7. The common injection device as claimed in claim 6, characterized in that the angular displacement drive has a structure with at least one turning-angle limiting tooth, the angular displacement drive sets the number of the turning-angle limiting teeth according to the information corresponding to the drug contained in the injection needle, the driven wheel of the electronic reading module is a gear that engages the turning-angle limiting teeth, the angular displacement detection element is selected from a potentiometer or a variable resistor and is electrically connected to the control circuit board of the control assembly, a specific rotation angle range is provided as the contact transmission section by the turning-angle limiting teeth, an area on a periphery of the angular displacement drive is a non-contact transmission section, and the angular displacement detection element outputs a corresponding voltage signal to the control circuit board according to the angular displacement of the driven wheel driven to rotate.

8. The common injection device as claimed in claim 6, characterized in that the contact transmission section of the angular displacement drive has frictional resistance, a specific length is set according to the information corresponding to the drug contained in the injection needle, the driven wheel of the electronic reading module is a friction wheel that is frictionally driven by the angular displacement drive, the angular displacement detection element is selected from a potentiometer or a variable resistor and is electrically connected to the control circuit board of the control assembly, and the angular displacement detection element outputs a corresponding voltage signal to the control circuit board according to the angular displacement of the driven wheel driven to rotate.

9. The common injection device as claimed in claim 5, characterized in that the injection propulsion mechanism is an electric injection propulsion mechanism and comprises:

a casing having a front end detachably connected to the connecting portion of the needle bushing;

a screw push rod set disposed in the casing and driven to extend out of the front end of the casing to insert into the injection needle to provide the pushing force;

an electric motor disposed in the casing and connected to the screw push rod set; and a control assembly disposed in the casing and having a control circuit board with a microprocessor and a switch element, the control circuit board electrically connected to the electric motor to determine an operation mode of the electric motor, and the switch element disposed out of the casing to control switching on or off the control circuit board;

wherein the electronic reading module is an angular displacement analog module and has a conductive coating or a conductive sticker formed on a specific section of the outer surface of the connecting portion of the needle bushing, the electronic reading module has an angular displacement detection element, the angular displacement detection element has a coil and is electrically connected to the control circuit board of the control assembly, the angular displacement detection element detects a magnetic flux change according to a distance change of the conductive coating or the conductive sticker due to a rotational angular displacement and outputs a corresponding magnetic flux signal to the control circuit board, and the microprocessor of the control circuit board reads the corresponding magnetic flux signal to determine the kind of the drug and to decide to execute a specific injection propelling action corresponding to the drug.

10. The common injection device as claimed in claim 5, characterized in that the injection propulsion mechanism is an electric injection propulsion mechanism and comprises:

a casing having a front end detachably connected to the connecting portion of the needle bushing;

a screw push rod set disposed in the casing and driven to extend out of the front end of the casing to insert into the injection needle to provide the pushing force;

an electric motor disposed in the casing and connected to the screw push rod set; and a control assembly disposed in the casing and having a control circuit board with a microprocessor and a switch element, the control circuit board electrically connected to the electric motor to determine an operation mode of the electric motor, and the switch element disposed out of the casing to control switching on or off the control circuit board;

wherein the drug-information providing portion provides photoelectric coding digital information and has a light sensing section whose specific light transmission area is set according to the information corresponding to the drug contained in the injection needle, the electronic reading module is a photoelectric coding module, is disposed in the casing of the injection propulsion mechanism and has a light source and a light detection element, the light source and the light detection element are located on two opposite sides of the light sensing section and are electrically connected to the control circuit board of the control assembly, the light detection element senses the transmittance of the light emitted by the light source through the light sensing section and outputs a corresponding voltage signal to the control circuit board, and the microprocessor of the control circuit board determines the kind of drug and decides to perform a specific injection propulsion action corresponding to the drug.

11. The common injection device as claimed in claim 5, characterized in that the injection propulsion mechanism is an electric injection propulsion mechanism and comprises:
- a casing having a front end detachably connected to the connecting portion of the needle bushing;
- a screw push rod set disposed in the casing and driven to extend out of the front end of the casing to insert into the injection needle to provide the pushing force;
- an electric motor disposed in the casing and connected to the screw push rod set; and
- a control assembly disposed in the casing and having a control circuit board with a microprocessor and a switch element, the control circuit board electrically connected to the electric motor to determine an operation mode of the electric motor, and the switch element disposed out of the casing to control switching on or off the control circuit board;
- wherein the drug-information providing portion has a one-dimensional barcode or a two-dimensional barcode set according to the information corresponding to the drug contained in the injection needle, the electronic reading module is disposed in the casing of the injection propulsion mechanism and has a light source and an image scanning element, the light source and the image scanning element are electrically connected to the control circuit board, the light source emits light on the drug-information providing portion, the image scanning element scans the one-dimensional barcode or two-dimensional barcode of the drug-information providing portion, the microprocessor of the control circuit board determines the kind of the drug by information of scanning the one-dimensional barcode or two-dimensional barcode of the drug-information providing portion and decides to perform a specific injection propulsion action corresponding to the drug.

12. The common injection device as claimed in claim 4, characterized in that the control assembly further has a display screen and a control module with an operating lever, the display screen and the control module are disposed in the casing and are both electrically connected to the control circuit board, and the display screen and the operating lever are exposed out of the casing.

13. The common injection device as claimed in claim 6, characterized in that the control assembly further has a display screen and a control module with an operating lever, the display screen and the control module are disposed in the casing and are both electrically connected to the control circuit board, and the display screen and the operating lever are exposed out of the casing.

14. The common injection device as claimed in claim 7, characterized in that the control assembly further has a display screen and a control module with an operating lever, the display screen and the control module are disposed in the casing and are both electrically connected to the control circuit board, and the display screen and the operating lever are exposed out of the casing.

15. The common injection device as claimed in claim 8, characterized in that the control assembly further has a display screen and a control module with an operating lever, the display screen and the control module are disposed in the casing and are both electrically connected to the control circuit board, and the display screen and the operating lever are exposed out of the casing.

16. The common injection device as claimed in claim 9, characterized in that the control assembly further has a display screen and a control module with an operating lever, the display screen and the control module are disposed in the casing and are both electrically connected to the control circuit board, and the display screen and the operating lever are exposed out of the casing.

17. The common injection device as claimed in claim 10, characterized in that the control assembly further has a display screen and a control module with an operating lever, the display screen and the control module are disposed in the casing and are both electrically connected to the control circuit board, and the display screen and the operating lever are exposed out of the casing.

18. The common injection device as claimed in claim 11, characterized in that the control assembly further has a display screen and a control module with an operating lever, the display screen and the control module are disposed in the casing and are both electrically connected to the control circuit board, and the display screen and the operating lever are exposed out of the casing.

\* \* \* \* \*